United States Patent
Meijer et al.

(10) Patent No.: US 10,610,385 B2
(45) Date of Patent: Apr. 7, 2020

(54) MULTI-MODAL UPPER LIMB PROSTHETIC DEVICE CONTROL USING MYOELECTRIC SIGNALS

(71) Applicant: TOUCH BIONICS LIMITED, Livingston (GB)

(72) Inventors: Robertus Meijer, Falkirk (GB); Kianoush Nazarpour, Edinburgh (GB)

(73) Assignee: Touch Bionics Limited, Livingston (GB)

(*) Notice: Subject to any disclaimer, the term of this patent is extended or adjusted under 35 U.S.C. 154(b) by 0 days.

(21) Appl. No.: 14/765,638

(22) PCT Filed: Feb. 5, 2014

(86) PCT No.: PCT/GB2014/050331
§ 371 (c)(1),
(2) Date: Aug. 4, 2015

(87) PCT Pub. No.: WO2014/122455
PCT Pub. Date: Aug. 14, 2014

(65) Prior Publication Data
US 2015/0374515 A1   Dec. 31, 2015

(30) Foreign Application Priority Data

Feb. 5, 2013 (GB) .................................. 1302025.0

(51) Int. Cl.
*A61F 2/72* (2006.01)
*A61F 2/58* (2006.01)
(Continued)

(52) U.S. Cl.
CPC ................ *A61F 2/72* (2013.01); *A61F 2/583* (2013.01); *A61F 2/586* (2013.01); *A61F 2/70* (2013.01);
(Continued)

(58) Field of Classification Search
CPC .... A61F 2/72; A61F 2002/6827; A61F 2/583; A61F 2/68; A61F 2002/769; A61F 2/70; A61F 2002/7615; B25J 13/087
See application file for complete search history.

(56) References Cited

U.S. PATENT DOCUMENTS 1,507,682 A    9/1924  Pecorella et al.
2,445,711 A    7/1948  Fitch
(Continued)

FOREIGN PATENT DOCUMENTS

CN    1803413       7/2006
CN    106994694     8/2017
(Continued)

OTHER PUBLICATIONS

Connolly, "Prosthetic hands from Touch Bionics," Industrial Robot: An International Journal, 35(4):290-293, 2008.
(Continued)

*Primary Examiner* — Christie L Bahena
(74) *Attorney, Agent, or Firm* — Knobbe, Martens, Olson & Bear, LLP

(57) ABSTRACT

Methods of operating a prosthesis (10*a*) having at least one moveable component (12) and an electronic control device (18) are provided, where the at least one moveable component (12) has two or more operating modes (30) and at least one operating parameter (28). The method comprises receiving at least one input control signal (p1,p2,pn) from the wearer of the prosthesis (10*a*), comparing the at least one input control signal (p1,p2,pn) with an operating profile (26) stored in the electronic control device in order to determine a desired operating mode (30) and operating parameter (28), and instructing the moveable component (12) to move in accordance with the desired operating mode (30) and operating parameter (28). Prostheses are also provided, at least one such prosthesis (10*a*) comprising at least one moveable
(Continued)

component (12) and an electronic device (18) operable to select both an operating mode (30) of the at least one moveable component (12) and at least one operating parameter (28) of the at least one moveable component (12) in response to an input command signal (P) from the wearer of the prosthesis.

16 Claims, 11 Drawing Sheets

(51) Int. Cl.
  *A61F 2/70* (2006.01)
  *A61F 2/68* (2006.01)

(52) U.S. Cl.
  CPC . *A61F 2002/587* (2013.01); *A61F 2002/6827* (2013.01); *A61F 2002/701* (2013.01); *A61F 2002/704* (2013.01)

(56) References Cited

U.S. PATENT DOCUMENTS

| | | | |
|---|---|---|---|
| 2,477,463 A | 7/1949 | Otterman | |
| 2,482,555 A | 9/1949 | Otterman | |
| 2,508,156 A | 5/1950 | Gillman | |
| 2,516,791 A | 7/1950 | Motis et al. | |
| 2,592,842 A | 4/1952 | Alderson | |
| 2,669,727 A | 2/1954 | Opuszenski | |
| 2,983,162 A | 5/1961 | Musser | |
| 3,406,584 A | 10/1968 | Roantree | |
| 3,509,583 A | 5/1970 | Fraioli | |
| 3,683,423 A | 8/1972 | Crapanzano | |
| 3,751,995 A | 8/1973 | Carlson | |
| 3,837,010 A | 9/1974 | Prout | |
| 3,866,246 A | 2/1975 | Seamone et al. | |
| 3,883,900 A | 5/1975 | Jerard et al. | |
| 3,922,930 A | 12/1975 | Fletcher et al. | |
| 4,030,141 A * | 6/1977 | Graupe | A61F 2/68 623/25 |
| 4,044,274 A | 8/1977 | Ohm | |
| 4,114,464 A | 9/1978 | Schubert et al. | |
| 4,197,592 A | 4/1980 | Klein | |
| 4,398,110 A | 8/1983 | Flinchbaugh et al. | |
| 4,558,704 A | 12/1985 | Petrofsky | |
| 4,577,127 A | 3/1986 | Ferree et al. | |
| 4,623,354 A | 11/1986 | Childress et al. | |
| 4,678,952 A | 7/1987 | Peterson et al. | |
| 4,808,187 A | 2/1989 | Patterson et al. | |
| 4,813,303 A | 3/1989 | Beezer et al. | |
| 4,822,238 A | 4/1989 | Kwech | |
| 4,955,918 A | 9/1990 | Lee | |
| 4,960,425 A | 10/1990 | Yan et al. | |
| 4,990,162 A | 2/1991 | LeBlanc et al. | |
| 5,020,162 A | 6/1991 | Kersten et al. | |
| 5,062,673 A | 11/1991 | Mimura | |
| 5,088,125 A | 2/1992 | Ansell et al. | |
| 5,133,775 A | 7/1992 | Chen | |
| 5,246,463 A | 9/1993 | Giampapa | |
| 5,252,102 A | 10/1993 | Singer et al. | |
| 5,255,188 A | 10/1993 | Telepko | |
| 5,387,245 A | 2/1995 | Fay et al. | |
| 5,413,454 A | 5/1995 | Movsesian | |
| 5,413,611 A | 5/1995 | Haslam, II et al. | |
| 5,498,472 A | 3/1996 | Gold | |
| 5,501,498 A | 3/1996 | Ulrich | |
| 5,581,166 A | 12/1996 | Eismann et al. | |
| 5,785,960 A | 7/1998 | Rigg et al. | |
| 5,851,194 A | 12/1998 | Fratrick | |
| 5,852,675 A | 12/1998 | Matsuo et al. | |
| 5,888,213 A * | 3/1999 | Sears | A61F 2/68 623/24 |
| 5,888,246 A | 3/1999 | Gow | |
| 5,900,714 A | 5/1999 | Dubhashi et al. | |
| 6,111,973 A | 8/2000 | Holt et al. | |
| 6,175,962 B1 | 1/2001 | Michelson | |
| 6,223,615 B1 | 5/2001 | Huck | |
| 6,244,873 B1 * | 6/2001 | Hill | G06F 3/015 379/110.01 |
| 6,344,062 B1 | 2/2002 | Abboudi et al. | |
| 6,361,570 B1 | 3/2002 | Gow | |
| 6,660,043 B2 | 12/2003 | Kajitani et al. | |
| 6,786,112 B2 | 9/2004 | Ruttor | |
| 7,144,430 B2 | 12/2006 | Archer et al. | |
| 7,243,569 B2 | 7/2007 | Takahashi et al. | |
| 7,316,304 B2 | 1/2008 | Heravi et al. | |
| 7,316,795 B1 | 1/2008 | Knauss | |
| 7,370,896 B2 | 5/2008 | Anderson et al. | |
| 7,640,680 B1 | 1/2010 | Castro | |
| 7,823,475 B2 | 11/2010 | Hirabayashi et al. | |
| 7,867,287 B2 | 1/2011 | Puchhammer | |
| 7,922,773 B1 | 4/2011 | Kuiken | |
| 8,016,893 B2 | 9/2011 | Weinberg et al. | |
| 8,100,986 B2 | 1/2012 | Puchhammer et al. | |
| 8,197,554 B2 | 6/2012 | Whiteley et al. | |
| 8,257,446 B2 | 9/2012 | Puchhammer | |
| 8,337,568 B2 | 12/2012 | Macduff | |
| 8,491,666 B2 | 7/2013 | Schulz | |
| 8,579,991 B2 | 11/2013 | Puchhammer | |
| 8,593,255 B2 | 11/2013 | Pang et al. | |
| 8,657,887 B2 | 2/2014 | Gill | |
| 8,662,552 B2 | 3/2014 | Torres-Jara | |
| 8,663,339 B2 | 3/2014 | Inschlag et al. | |
| 8,690,963 B2 | 4/2014 | Puchhammer | |
| 8,696,763 B2 | 4/2014 | Gill | |
| 8,808,397 B2 | 8/2014 | Gow | |
| 8,828,096 B2 | 9/2014 | Gill | |
| 8,986,395 B2 | 3/2015 | McLeary | |
| 8,995,760 B2 | 3/2015 | Gill | |
| 9,278,012 B2 | 3/2016 | Gill | |
| 9,387,095 B2 | 7/2016 | McLeary et al. | |
| 9,402,749 B2 | 8/2016 | Gill et al. | |
| 9,463,100 B2 | 10/2016 | Gill | |
| 9,720,515 B2 | 8/2017 | Wagner et al. | |
| 9,839,534 B2 | 12/2017 | Lipsey et al. | |
| 9,999,522 B2 | 6/2018 | Gill | |
| 10,265,197 B2 | 4/2019 | Gill et al. | |
| 10,318,863 B2 | 6/2019 | Lock et al. | |
| 10,369,016 B2 | 8/2019 | Lipsey et al. | |
| 10,369,024 B2 | 8/2019 | Gill | |
| 10,398,576 B2 | 9/2019 | Gill et al. | |
| 10,449,063 B2 | 10/2019 | Gill | |
| 2001/0023058 A1 | 9/2001 | Jung et al. | |
| 2002/0016631 A1 | 2/2002 | Marchitto et al. | |
| 2002/0135241 A1 | 9/2002 | Kobayashi et al. | |
| 2002/0143405 A1 * | 10/2002 | Davalli | A61F 2/68 623/24 |
| 2003/0036805 A1 | 2/2003 | Senior | |
| 2004/0002672 A1 | 1/2004 | Carlson | |
| 2004/0078091 A1 | 4/2004 | Elkins | |
| 2004/0078299 A1 | 4/2004 | Down-Logan et al. | |
| 2004/0181289 A1 | 9/2004 | Bedard et al. | |
| 2004/0182125 A1 | 9/2004 | McLean | |
| 2005/0021154 A1 | 1/2005 | Brimalm | |
| 2005/0021155 A1 | 1/2005 | Brimalm | |
| 2005/0093997 A1 | 5/2005 | Dalton et al. | |
| 2005/0101693 A1 | 5/2005 | Arbogast et al. | |
| 2005/0192677 A1 | 9/2005 | Ragnarsdottir et al. | |
| 2006/0029909 A1 | 2/2006 | Kaczkowski | |
| 2006/0054782 A1 | 3/2006 | Olsen et al. | |
| 2006/0158146 A1 | 7/2006 | Tadano | |
| 2006/0167564 A1 | 7/2006 | Flaherty et al. | |
| 2006/0212129 A1 | 9/2006 | Lake et al. | |
| 2006/0229755 A1 | 10/2006 | Kuiken et al. | |
| 2006/0251408 A1 | 11/2006 | Konno et al. | |
| 2007/0032884 A1 | 2/2007 | Veatch | |
| 2007/0058860 A1 | 3/2007 | Harville et al. | |
| 2007/0061111 A1 | 3/2007 | Jung et al. | |
| 2007/0071314 A1 | 3/2007 | Bhatti et al. | |
| 2007/0175681 A1 | 8/2007 | King et al. | |
| 2007/0230832 A1 | 10/2007 | Usui et al. | |
| 2007/0260328 A1 | 11/2007 | Bertels et al. | |
| 2008/0058668 A1 * | 3/2008 | Seyed Momen | A61B 5/04888 600/546 |

(56) References Cited

U.S. PATENT DOCUMENTS

| | | | |
|---|---|---|---|
| 2008/0146981 | A1 | 6/2008 | Greenwald et al. |
| 2008/0215162 | A1 | 9/2008 | Farnsworth et al. |
| 2008/0260218 | A1 | 10/2008 | Smith et al. |
| 2008/0262634 | A1 | 10/2008 | Puchhammer |
| 2009/0213379 | A1 | 8/2009 | Carroll et al. |
| 2010/0016990 | A1 | 1/2010 | Kurtz |
| 2010/0116078 | A1 | 5/2010 | Kim |
| 2010/0274365 | A1 | 10/2010 | Evans et al. |
| 2011/0203027 | A1 | 8/2011 | Flather et al. |
| 2011/0237381 | A1 | 9/2011 | Puchhammer |
| 2011/0257765 | A1 | 10/2011 | Evans et al. |
| 2011/0264238 | A1 | 10/2011 | van der Merwe et al. |
| 2011/0265597 | A1 | 11/2011 | Long |
| 2011/0278061 | A1 | 11/2011 | Farnan |
| 2012/0004884 | A1 | 1/2012 | Fillol et al. |
| 2012/0014571 | A1 | 1/2012 | Wong et al. |
| 2012/0061155 | A1 | 3/2012 | Berger et al. |
| 2012/0099788 | A1 | 4/2012 | Bhatti et al. |
| 2012/0109337 | A1 | 5/2012 | Schulz |
| 2012/0123558 | A1 | 5/2012 | Gill |
| 2012/0204665 | A1 | 8/2012 | Baudasse |
| 2012/0280812 | A1 | 11/2012 | Sheikman et al. |
| 2012/0286629 | A1 | 11/2012 | Johnson et al. |
| 2012/0303136 | A1 | 11/2012 | Macduff |
| 2012/0330439 | A1 | 12/2012 | Goldfarb et al. |
| 2013/0041476 | A1 | 2/2013 | Schulz |
| 2013/0053984 | A1 | 2/2013 | Hunter et al. |
| 2013/0076699 | A1 | 3/2013 | Spencer |
| 2013/0144197 | A1 | 6/2013 | Ingimundarson et al. |
| 2013/0253705 | A1* | 9/2013 | Goldfarb .............. A61F 2/583 700/260 |
| 2013/0268094 | A1 | 10/2013 | Van Wiemeersch |
| 2014/0236314 | A1 | 8/2014 | Van Wiemeersch |
| 2014/0324189 | A1 | 10/2014 | Gill et al. |
| 2014/0371871 | A1 | 12/2014 | Farina et al. |
| 2015/0142082 | A1 | 5/2015 | Simon et al. |
| 2015/0216679 | A1 | 8/2015 | Lipsey et al. |
| 2015/0216681 | A1 | 8/2015 | Lipsey et al. |
| 2015/0230941 | A1 | 8/2015 | Jury |
| 2015/0351935 | A1 | 12/2015 | Donati et al. |
| 2016/0250044 | A1 | 9/2016 | Iversen et al. |
| 2016/0287422 | A1 | 10/2016 | Kelly et al. |
| 2017/0007424 | A1 | 1/2017 | Gill |
| 2017/0049586 | A1 | 2/2017 | Gill et al. |
| 2017/0281368 | A1 | 10/2017 | Gill |
| 2018/0064563 | A1 | 3/2018 | Gill |
| 2018/0071115 | A1 | 3/2018 | Lipsey et al. |
| 2018/0296368 | A1 | 10/2018 | Gill |
| 2019/0091040 | A1 | 3/2019 | Gill |
| 2019/0183661 | A1 | 6/2019 | Gill |
| 2019/0216618 | A1 | 7/2019 | Gill |

FOREIGN PATENT DOCUMENTS

| | | |
|---|---|---|
| DE | 309 367 | 11/1918 |
| DE | 24 34 834 | 2/1976 |
| DE | 198 54 762 | 6/2000 |
| DE | 101 05 814 | 9/2002 |
| DE | 203 15 575 | 1/2004 |
| DE | 10 2012 009 699 | 11/2013 |
| EP | 0145504 | 6/1985 |
| EP | 0 219 478 | 4/1987 |
| EP | 0 256 643 | 2/1988 |
| EP | 0 484 173 | 5/1992 |
| EP | 0 947 899 | 10/1999 |
| EP | 0 968 695 | 1/2000 |
| EP | 1043003 | 10/2000 |
| EP | 1 617 103 | 1/2006 |
| EP | 2 532 927 | 12/2012 |
| EP | 2 612 619 | 7/2013 |
| EP | 2 653 137 | 10/2013 |
| GB | 326 970 | 3/1930 |
| GB | 607 001 | 2/1947 |
| GB | 1 386 942 | 3/1975 |
| GB | 1 510 298 | 5/1978 |
| GB | 1585256 | 2/1981 |
| GB | 2 067 074 | 7/1981 |
| GB | 2 146 406 | 4/1985 |
| GB | 2 357 725 | 7/2001 |
| GB | 2444679 | 6/2008 |
| JP | 53-11456 | 2/1978 |
| JP | 53-094693 | 8/1978 |
| JP | 07-174631 | 7/1995 |
| JP | 2001-082913 | 3/2001 |
| JP | 2001-299448 | 10/2001 |
| JP | 2002-131135 | 5/2002 |
| JP | 2002-310242 | 10/2002 |
| JP | 2003-134526 | 5/2003 |
| JP | 2004-073802 | 3/2004 |
| JP | 2004-224280 | 8/2004 |
| WO | 95/24875 | 9/1995 |
| WO | WO 96/023643 | 8/1996 |
| WO | WO 00/025840 | 5/2000 |
| WO | 00/69375 | 11/2000 |
| WO | WO 01/004838 | 1/2001 |
| WO | WO 02/049534 | 6/2002 |
| WO | 03/017878 | 3/2003 |
| WO | 03/017880 | 3/2003 |
| WO | WO 03/017877 | 3/2003 |
| WO | 2006/069264 | 6/2006 |
| WO | WO 2006/058190 | 6/2006 |
| WO | WO 2006/078432 | 7/2006 |
| WO | WO 2006/086504 | 8/2006 |
| WO | WO 2006/092604 | 9/2006 |
| WO | WO 2006/110790 | 10/2006 |
| WO | 2007/063266 | 6/2007 |
| WO | 2007/076764 | 7/2007 |
| WO | 2007/076765 | 7/2007 |
| WO | 2007/127973 | 11/2007 |
| WO | WO 2007/126854 | 11/2007 |
| WO | 2008/044207 | 4/2008 |
| WO | WO 2008/044052 | 4/2008 |
| WO | 2008/098059 | 8/2008 |
| WO | 2008/098072 | 8/2008 |
| WO | WO 2008/092695 | 8/2008 |
| WO | WO 2009/011682 | 1/2009 |
| WO | 2010/018358 | 2/2010 |
| WO | WO 2010/051798 | 5/2010 |
| WO | WO 2010/149967 | 12/2010 |
| WO | 2011/001136 | 1/2011 |
| WO | 2011/022569 | 2/2011 |
| WO | 2011/036473 | 3/2011 |
| WO | WO 2011/036626 | 3/2011 |
| WO | WO 2011/088964 | 7/2011 |
| WO | 2011/107778 | 9/2011 |
| WO | WO 2011/143004 | 11/2011 |
| WO | WO 2015/120076 | 8/2015 |
| WO | WO 2015/120083 | 8/2015 |
| WO | WO 2016/051138 | 4/2016 |
| WO | WO 2017/061879 | 4/2017 |

OTHER PUBLICATIONS

Stix, "Phantom Touch: Imbuing a Prosthesis with Manual Dexterity," Scientific American, Oct. 1998, pp. 41 and 44.

Search Report for GB Application No. GB0916895.6 dated Mar. 17, 2010, 5 pages.

Search Report for GB Application No. GB0910920.8 dated Mar. 26, 2010, 3 pages.

PCT International Search Report for PCT International Application No. PCT/GB2013/051961, dated Dec. 11, 2013, 5 pages.

PCT International Search Report for PCT International Application No. PCT/GB2012/052021, dated Nov. 26, 2012, 5 pages.

PCT Written Opinion of the International Searching Authority for PCT International Application No. PCT/GB2012/052021, dated May 3, 2013, 6 pages.

PCT International Search Report for PCT International Application No. PCT/GB2012/052111, dated Nov. 26, 2012, 5 pages.

PCT International Preliminary Report on Patentability for PCT International Application No. PCT/GB2010/051529, dated Apr. 5, 2012, 7 pages.

(56) References Cited

OTHER PUBLICATIONS

PCT International Preliminary Report on Patentability for PCT International Application No. PCT/GB2011/050368, dated Sep. 13, 2012, 7 pages.

PCT International Search Report and Written Opinion of International Searching Authority for PCT International Application No. PCT/GB2011/050368, dated Jun. 21, 2011, 11 pages.

PCT International Search Report and Written Opinion of International Searching Authority for PCT International Application No. PCT/GB2010/001232, dated Oct. 6, 2010, 9 pages.

PCT International Preliminary Report on Patentability for PCT International Application No. PCT/GB2010/001232, dated Jan. 4, 2012, 6 pages.

PCT International Search Report and Written Opinion of International Searching Authority for PCT International Application No. PCT/GB2010/051529, dated Jan. 4, 2011, 11 pages.

Ernesto C. Martinez-Villalpando "Agonist-antagonist active knee prosthesis: A preliminary study in level-ground walking" Journal of Rehabilitation Research & Development, vol. 46, No. 3, (2009), pp. 361-374.

Matthew S. Trachtenberg et al. "Radio frequency identification, An innovative solution to guide dexterous prosthetic hands" 33rd Annual International Conference of the IEEE EMBS, Boston, Massachusetts, USA, [Aug. 30-Sep. 3, 2011], 4 pages.

Luke Osborn et al. "Utilizing tactile feedback for biomimetic grasping control in upper limb prostheses" Department of Biomedical Engineering, Johns Hopkins University, Baltimore, USA, [2013], 4 pages.

Alessandra Pedrocchi et al. "MUNDUS project: Multimodal Neuroprosthesis for daily Upper Limb Support" Journal of Neuroengineering and Rehabilitation, [2013], 10:66, http://www.jneuroengrehab.com/content/10/1/66, 20 pages.

Michael Mace et al. "Augmenting neuroprosthetic hand control through evaluation of a bioacoustic interface" IEEE/RSJ International Conference on Intelligent Robots and Systems (IROS), Tokyo, Japan, [Nov. 3-7, 2013], 7 pages.

Albu-Schaffer et al., "Soft Robotics", IEEE Robot. Autom. Mag., 2008, vol. 15, No. 3, pp. 20-30.

Bellman et al., "SPARKy 3: Design of an Active Robotic Ankle Prosthesis with Two Actuated Degrees of Freedom Using Regenerative Kinetics", in Proc. IEEE/RAS-EMBS Int. Conf. Biomed. Robot. Biomechatron., 2008, pp. 511-516.

Belter et al., "Mechanical Design and Performance Specifications of Anthropomorphic Prosthetic Hands: A Review", URRD, Jan. 2013, vol. 50, No. 5, pp. 599-618.

Biddiss et al., "Consumer Design Priorities for Upper Limb Prosthetics," Disabil. Rehabil. Assist. Technol., Jan. 2007, vol. 2, No. 6, pp. 346-357.

Biddiss et al., "Upper Limb Prosthesis Use and Abandonment: A Survey of the Last 25 Years", Prosthetics Orthotics Int., 2007, vol. 31, No. 3, pp. 236-257.

Biddiss et al., "Upper-Limb Prosthetics: Critical Factors in Device Abandonment", Amer. J. Phys. Med. Rehabil., Dec. 2007, vol. 86, No. 12, pp. 977-987.

Chicoine et al., "Prosthesis-Guided Training of Pattern Recognition-Controlled Myoelectric Prosthesis", in Proc. IEEE Annu. Int. Conf. Eng. Med. Biol. Soc., 2012, vol. 60611, pp. 1876-1879.

Childress et al., "Control of Limb Prostheses", Atlas of Amputations and Limb Deficiencies, D. G. Smith, J. W. Michael, and J. H. Bowker, Eds., 3rd ed. Rosemont, IL, USA: American Academy of Orthopaedic Surgeons, 2004.

Choi et al., "Design of High Power Permanent Magnet Motor with Segment Rectangular Copperwire and Closed Slot Opening on Electric Vehicles", IEEE Trans. Magn., Jun. 2010, vol. 46, No. 9, pp. 3701-3704.

Cipriani et al., "On the Shared Control of an EMG-Controlled Prosthetic Hand: Analysis of User-Prosthesis Interaction", IEEE Trans. Robot., Feb. 2008, vol. 24, No. 1, pp. 170-184.

Controzzi et al., "Miniaturized Nonback-Drivable Mechanism for Robotic Applications", Mech. Mach. Theory, Oct. 2010, vol. 45, No. 10, pp. 1395-1406.

Damian et al., "Artificial Tactile Sensing of Position and Slip Speed by Exploiting Geometrical Features", IEEE Trans. Mechatronics, Feb. 2015, vol. 20, No. 1, pp. 263-274.

Dechev et al., "Multiple Finger, Passive Adaptive Grasp Prosthetic Hand", Mechanism and Machine Theory, Oct. 1, 2001, vol. 36, No. 10, pp. 1157-1173.

Dellorto, Danielle, "Bionic Hands Controlled by iPhone App", CNN, Apr. 12, 2013, pp. 4 http://www.cnn.com/2013/04/12/health/bionic-hands.

"DuPont Engineering Design—The Review of DuPont Engineering Polymers in Action", http://www.engpolymer.co.kr/x_data/magazine/engdesign07_2e.pdf, 2007, pp. 16.

Engeberg et al., "Adaptive Sliding Mode Control for Prosthetic Hands to Simultaneously Prevent Slip and Minimize Deformation of Grasped Objects," IEEE/ASME Trans. Mechatronics, Feb. 2013, vol. 18, No. 1, pp. 376-385.

Fougner et al., "Control of Upper Limb Prostheses: Terminology and Proportional Myoelectric Control—A Review", IEEE Trans. Neural Syst. Rehabil. Eng., Sep. 2012, vol. 20, No. 5, pp. 663-677.

Gaine et al., "Upper Limb Traumatic Amputees. Review of Prosthetic Use", J. Hand Surg. Amer. 1997, vol. 22 B, No. 1, pp. 73-76.

Heckathorne et al., "Components for Electric-Powered Systems", in Atlas of Amputations and Limb Deficiencies, 3rd Ed. Rosemont, IL, USA: American Academy of Orthopaedic Surgeons, 2004, pp. 145-172.

Hojjat et al., "A Comprehensive Study on Capabilities and Limitations of Roller-Screw with Emphasis on Slip Tendency", Mech. Mach. Theory, 2009, vol. 44, No. 10, pp. 1887-1899.

Hsieh et al., "Dynamics Analysis of Cycloidal Speed Reducers with Pinwheel and Nonpinwheel Designs", ASME J. Mech. Des. Jun. 2014, vol. 136, No. 9, p. 091008.

Jebsen et al., "An Objective and Standardized Test of Hand Function", Arch. Phys. Med. Rehabil., 1969, vol. 50, No. 6, pp. 311-319.

Johannes et al., "An Overview of the Developmental Process for the Modular Prosthetic Limb," John Hopkins APL Tech.Dig., 2011, vol. 30, No. 3, pp. 207-216.

Kent et al., "Electromyogram Synergy Control of a Dexterous Artificial Hand to Unscrew and Screw Objects", J. Neuroeng. Rehabil. 2014, vol. 11, No. 1.

Kermani et al., "Friction Identification and Compensation in Robotic Manipulators", IEEE Trans. Instrum. Meas., Dec. 2007, vol. 56, No. 6, pp. 2346-2353.

Kuiken et al., "Targeted Muscle Reinnervation for Real-Time Myoelectric Control of Multifunction Artificial Arms", JAMA, Feb. 11, 2009, vol. 301, No. 6, pp. 619-628.

Light et al., "Establishing a Standarized Clinical Assessment Tool of Pathologic and Prosthetic Hand Function: Normative Data, Reliability, and Validity", Arch. Phys. Med. Rehabil., 2002, vol. 83, pp. 776-783.

Majd et al., "A Continuous Friction Model for Servo Systems with Stiction", in Proc. Int. Conf. Control Appl., 1995, pp. 296-301.

Maxon Precision Motors, Inc., "Maxon Flat Motor: EX 10 flat 10 mm, brushless, 0.25 Watt", Specification, May 2011, p. 181.

Maxon Precision Motors, Inc., "Maxon EX Motor: EC10 10 mm, brushless, 8 Watt", Specification, May 2011, p. 140.

Miller et al., "Summary and Recommendations of the Academy's Staty of the Science Conference on Upper Limb Prosthetic Outcome Measures", J. Prosthetics Orthotics, 2009, vol. 21, pp. 83-89.

Montagnani et al., "Is it Finger or Wrist Dexterity that is Missing in Current Hand Prostheses?" IEEE Trans. Neural Syst. Rehabil. Eng., Jul. 2015, vol. 23, No. 4, pp. 600-609.

Morita et al., "Development of 4-D.O.F. Manipulator Using Mechanical Impedance Adjuster", in Proc. IEEE Int. Conf. Robot. Autom., 1996, pp. 2902-2907.

Ninu et al., "Closed-Loop Control of Grasping with a Myoelectric Hand Prosthesis: Which are the Relevant Feedback Variable for Force Control?" IEEE Trans. Neural Syst. Rehabil. Eng., Sep. 2014, vol. 22, No. 5, pp. 1041-1052.

(56) References Cited

OTHER PUBLICATIONS

Pinzur et al., "Functional Outcome Following Traumatic Upper Limb Amputation and Prosthetic Limb Fitting", J. Hand Surgery, Amer. vol. 1994. vol. 19, pp. 836-839.
Press Release, "Touch Bionics Introduce Digitally Controlled Supro Wrist", http://www.touchbionics.com/news-events/news/touch-bionics-introduce-digitally-controlled-supro-wrist, May 3, 2016 in 2 pages.
Raspopovic et al., "Restoring Natural Sensory Feedback in Real-Time Bidirectional Hand Prostheses", Sci. Transl. Med., 2014, vol. 6, No. 222.
Resnik et al., "The DEKA Arm: Its Features, Functionality, and Evolution During the Veterans Affairs Study to Optimize the DEKA Arm", Prosthetics Orthotics Int., 2014, vol. 38, pp. 492-504.
Scheme et al., "Electromyogram Pattern Recognition for Control of Powered Upper-Limb Prostheses: State of the Art and Challenges for Clinical Use", J. Rehabil. Res. Dev., 2011, vol. 48, No. 6, pp. 643-659.
Scheme et al., "Motion Normalized Proportional Control for Improved Pattern Recognition-Based Myoelectric Control", IEEE Trans. Neural Syst. Rehabil. Eng., Jan. 2014, vol. 22, No. 1, pp. 149-157.
Sensinger et al., "Cycloid vs. Harmonic Drives for use in High Ratio, Single Stage Robotic Transmissions", presented at the IEEE Conf. Robot. Autom. SI. Paul, MN, USA, 2012.
Sensinger, "Efficiency of High-Sensitivity Gear Trains, such as Cycloid Drives", J. Mech. Des., 2013, vol. 135, No. 7, p. 71006.
Sensinger et al., "Exterior vs. Interior Rotors in Robotic Brushless Motors", 2011 IEEE International Conference on Robotics and Automation (ICRA), IEEE, May 9, 2011, pp. 2764-2770.
Sensinger, "Selecting Motors for Robots Using Biomimetic Trajectories:Optimum Benchmarks, Windings, and other Considerations," in Proc. IEEE Conf. Robot. Autom., Anchorage, AL, USA, 2010, pp. 4175-4181.
Sensinger, "Unified Approach to Cycloid Drive Profile, Stress, and Efficiency Optimization", Journal of Mechanical Design, Feb. 2010, vol. 132, pp. 024503-1-024503-5.
Sensinger et al., "User-Modulated Impedance Control of a Prosthetic Elbow in Unconstrained, Perturbed Motion", IEEE Trans. Biomed. Eng., Mar. 2008, vol. 55, No. 3, pp. 1043-1055.
Sutton et al., "Towards a Universal Coupler Design for Modern Powered Prostheses", Presented at the Myoelect. Controls Symp., Fredericton, NB, Canada, 2011.
Tan et al., "A Neural Interface Provides Long-Term Stable Natural Touch Perception", Science Translational Medicine, Oct. 8, 2014, vol. 6, No. 257, pp. 1-11.
Tang, "General Concepts of Wrist Biomechanics and a View from Other Species", J. Hand Surg., Eur. vol., Aug. 2008, vol. 33, No. 4, pp. 519-525.
Toledo et al., "A Comparison of Direct and Pattern Recognition Control for a Two Degree-of-Freedom Above Elbow Virtual Prosthesis", in Proc. IEEE Annu. Int. Conf. Eng. Med. Biol. Soc., 2012, pp. 4332-4335.
Weir et al., "Design of Artificial Arms and Hands for Prosthetic Applications", Biomedical Engineering and Design Handbook, 2009, vol. 2, M. Kutz, Ed., 2nd Ed. New York, NY, USA: McGraw-Hill, pp. 537-598.
Wettels et al., "Grip Control Using Biomimetic Tactile Sensing Systems," IEEE/ASME Trans. Mechatronics, Dec. 2009, vol. 14, No. 6, pp. 718-723.
Whiteside et al., "Practice Analysis Task Force: Practice Analysis of the Disciplines of Orthotics and Prosthetics", American Board for Certification in Orthotics and Prosthetics, Inc., 2000, pp. 1-51.
Wilson et al., "A Bus-Based Smart Myoelectric Electrode/Amplifier-System Requirements", IEEE Trans. Instrum. Meas., Oct. 2011, vol. 60, No. 10, pp. 3290-3299.
Zampagni et al., "A Protocol for Clinical Evaluation of the Carrying Angle of the Elbow by Anatomic Landmarks", J. Shoulder Elbow Surg., 2008, vol. 17, No. 1, pp. 106-112.
"DC Circuit Theory", http://www.electronics-tutorials.ws/dccircuits/dco_1.html, Date verified by the Wayback Machine Apr. 23, 2013, pp. 16.
Grip Chips™, Datasheet, May 15, 2014, Issue 1, http://touchbionics.com/sites/default/files/files/Grip%20Chip%20datasheet%20May%202014.pdf, pp. 1.
International Preliminary Report on Patentability and Written Opinion in Application No. PCT/GB2014/050331, dated Aug. 20, 2015.
International Search Report and Written Opinion in Application No. PCT/GB2014/050331, dated May 8, 2014.
Kyberd et al., "Two-Degree-of-Freedom Powered Prosthetic Wrist", Journal of Rehabilitation Research & Development, 2011, vol. 48, No. 6, pp. 609-617.
"Touch Bionics Grip Chips Let Hand Prostheses Think for Themselves", May 15, 2014, www.medgadget.com/2014/05/touch-bionics-grip-chips-let-hand-prostheses-think-for-themselves.html, pp. 2.
Vilarino, Martin, "A Novel Wireless Controller for Switching among Modes for an Upper-Limb Prosthesis", The Academy TODAY, Jan. 2014, vol. 10, No. 1, pp. A-12 to A-15.
Antonio et al., "A Virtual Upper Limb Prosthesis as a Training System", 7th International Conference on Electrical Engineering, Computing Science and Automatic Control (CCE 2010) Tuxtla Gutiérrez, Chiapas, Mexico. Sep. 8-10, 2010, pp. 210-215.
Fukuda et al., "Training of Grasping Motion Using a Virtual Prosthetic Control System", 2010 IEEE International Conference on Systems Man and Cybernetics (SMC), Oct. 10-13, 2010, pp. 1793-1798.
Lamounier et al., "On the Use of Virtual and Augmented Reality for Upper Limb Prostheses Training and Simulation", 2010 Annual International Conference of the IEEE Engineering in Medicine and Biology Society (EMBC), Aug. 31-Sep. 4, 2010, pp. 2451-2454.
"Supro Wrist", Touch Bionics, https://web.archive.org/web/20160928141440/http://www.touchbionics.com/products/supro-wrist as archived Sep. 28, 2016 in 3 pages.
Touch Bionics PowerPoint Presentation in 3 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).
Touch Bionics PowerPoint Slide in 1 page, believed to be presented at Advanced Arm Dynamics company Jan. 11, 2016. (Applicant requests that the Examiner consider this reference as qualifying as prior art as of the date indicated, but Applicant does not admit its status as prior art by submitting it here and reserves the right to challenge the reference's prior art status at a later date).
Touch Bionics Screenshots of video in PowerPoint Presentation in 4 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).

* cited by examiner

MULTI-MODAL UPPER LIMB PROSTHETIC DEVICE CONTROL USING MYOELECTRIC SIGNALS

CROSS REFERENCE TO RELATED APPLICATIONS

This is the national phase under 35 U.S.C. § 371 of International Application No. PCT/GB2014/050331, filed on Feb. 5, 2014, which claims priority to and the benefit of Great Britain Patent Application No. 1302025.0, filed on Feb. 5, 2013, the entire disclosures of each of which are incorporated by reference herein.

The present invention relates to a prosthesis, particularly, but not exclusively, a hand prosthesis.

Prosthetic hands with powered digits are known. For example, WO 2007/063266 and WO 1995/24875 disclose a prosthesis with a mechanically operated digit member that is moved by an electric motor. The prosthesis is capable of operating in a number of modes, such as function modes (grasp, pinch, etc.) and gesture modes (point etc.).

It is an aim of the present invention to provide an improved prosthesis having a motor driven digit member.

According to a first aspect of the invention there is provided a method of operating a prosthesis having at least one moveable component and an electronic control device, the at least one moveable component having two or more operating modes and at least one operating parameter, the method comprising:
  receiving at least one input control signal from the wearer of the prosthesis;
  comparing the at least one input control signal with an operating profile stored in the electronic control device in order to determine a desired operating mode and operating parameter; and
  instructing the moveable component to move in accordance with the desired operating mode and operating parameter.

The method may further further comprise the steps of:
  storing input control signals received so as to establish an input control signal pattern; and
  predicting a desired operating mode and operating parameter based upon the input control signal pattern upon receiving the at least one control signal from the wearer of the prosthesis.

The method may further comprise a final step of sending a feedback signal to the wearer of the prosthesis, the feedback signal indicative of the selected operating mode and operating parameter.

The operating profile may be divided into a plurality of regions, each region representing a separate operating mode and operating parameter, and wherein the comparison step comprises plotting in one of the plurality of regions a resultant input command signal based upon the one or more input control signals, and determining the operating mode and operating parameter associated with that region.

The at least one input control signal may be generated by one or more sensors attached to the wearer of the prosthesis.

According to a second aspect of the invention there is provided a prosthesis comprising:
  at least one moveable component, the component having two or more operating modes and at least one operating parameter; and
  an electronic control device storing an operating profile; wherein the control device receives at least one input control signal from a wearer of the prosthesis, compares the at least one input control signal with the operating profile to determine a desired operating mode and operating parameter for the component, and instructs the component to move in accordance with the desired operating mode and operating parameter.

The electronic control device may include a memory for storing input control signals received so as to establish an input control signal pattern, and a program which predicts a desired operating mode and operating parameter based upon the input control signal pattern upon receiving the at least one control signal from the wearer of the prosthesis.

The electronic control device may include a signal generator which sends a feedback signal to the wearer of the prosthesis, the feedback signal indicative of the selected operating mode and operating parameter.

The prosthesis may further comprise one or more sensors attached to the wearer of the prosthesis for the generation of the at least one input control signal.

According to a third aspect of the invention there is provided a prosthesis comprising:
  at least one moveable component, wherein the at least one moveable component has two or more operating modes and at least one operating parameter; and
  an electronic device operable to select both an operating mode of the at least one moveable component and at least one operating parameter of the at least one moveable component in response to an input command signal from the wearer of the prosthesis.

The moveable component may be a digit of a hand prosthesis. The digit may be a finger or a thumb of a hand prosthesis. The digits may be moveable relative to a body part to which they are attached. The digits may be rotatably and/or pivotably moveable relative to a body part to which they are attached. The body part may be attachable to the wearer of the prosthesis.

The prosthesis may be configured such that it is attachable to a partial-hand amputee. That is, the prosthesis may be arranged such that it is attachable to a wearer who is missing one or more fingers or a thumb from their hand, with the moveable components replacing the missing fingers or thumb.

The moveable component may be a body part to which a digit may be attached. The moveable component may be a hand chassis. The moveable component may be a wrist or cuff component. The body part or hand chassis may be rotatably attachable to the wearer of the prosthesis.

The term operating mode is considered here to mean an operating movement of the moveable component in response to an input command signal from the wearer of the prosthesis. When the prosthesis comprises two or more moveable components, the term operating mode is considered to mean the operational interaction between the moveable components in response to an input command signal from the wearer of the prosthesis.

Each operating mode provides for a discrete operating movement of the moveable component. When the prosthesis comprises two or more moveable components, each operating mode provides for a discrete operational interaction between the moveable components. The operational interaction between the moveable components may include functional tasks that the wearer of the prosthesis wishes the components to perform, such as pressing the components together in a pinching action, or moving the components to a desired position to create a gesture, such as pointing.

The term operating parameter is considered here to mean an operating condition of the moveable component in response to an input command signal from the wearer of the prosthesis. The operating parameter of the moveable component may include its speed, acceleration, deceleration, force, operating duration, amount of extension, amount of flexion, angle of rotation etc.

The operating parameter of the moveable component may be proportional to the input command signal. That is, the operating condition of the moveable component may be proportional to the input command signal.

The electronic device may be operable to select both the operating mode of the at least one moveable component and the operating parameters of the moveable components in response to an input command signal from the wearer of the prosthesis.

The electronic device may be operable to simultaneously select both the operating mode of the at least one moveable component and at least one operating parameter of the at least one moveable component in response to an input command signal from the wearer of the prosthesis.

The electronic device may be operable to select both the operating mode of the at least one moveable component and the at least one operating parameter of at least one moveable component in response to a single input command signal from the wearer of the prosthesis.

The at least one moveable component may have a plurality of operating modes.

The prosthesis may comprise a plurality of moveable components. Each moveable component may have two or more operating modes and at least one operating parameter.

Each moveable component may have a plurality of operating parameters.

The electronic device may be operable to select one of the plurality of operating modes of the at least one moveable component and at least one operating parameter of the at least one moveable component in response to an input command signal from the wearer of the prosthesis.

The electronic device may be operable to select one of the plurality of operating modes of the at least one moveable component and at least one operating parameter of the at least one moveable component in response to a predetermined input command signal from the wearer of the prosthesis.

Each predetermined input command signal may result in selection of a corresponding predetermined operating mode of the at least one moveable component and at least one operating parameter of the at least one moveable component.

The input command signal may comprise two or more input signals from the wearer of the prosthesis. The input command signal may comprise a plurality of input signals from the wearer of the prosthesis.

The input signals from the wearer of the prosthesis may be provided via one or more switches. The switches may be analogue or digital switches. The switches may be actuated by residual movement of the wearer of the prosthesis, wrist and/or shoulder movement of the wearer of the prosthesis, movement of the remnant digits and/or knuckles, or the like.

The input signals from the wearer of the prosthesis may be provided by electrophysiological signals derived from the activity of, or from, surface electromyographic (EMG) and intramuscular activity of residual muscle actions of the wearer of the prosthesis, electroneurographic (ENG) activity of residual peripheral nerves of the wearer of the prosthesis, signals derived from one or more neural implants in the wearer of the prosthesis implanted in the brain or spinal cord, EMG activity from reinnervated muscles, muscles of the feet and/or chest, or the like.

The input signals from the wearer of the prosthesis may be provided by non-electrophysiological signals derived from the activity of pressure sensitive resistors on the wearer of the prosthesis, near infrared spectroscopy signal, or bend sensitive resistors on the wearer of the body to capture any residual movement of the digits, wrist, elbow or shoulder of the wearer of the prosthesis, or the like.

The input signals from the wearer of the prosthesis may be provided directly by signals derived from neural, spinal or muscular activity, for example, electromyographic (EMG) activity of hand muscle/forearm muscle actions, or residual muscle actions, of the wearer of the prosthesis recorded non-invasively from the surface of the skin or invasively from superficial or deep muscular structures with using needle or an array of needle electrodes. The prosthesis may be controlled by the activity of any combination of intrinsic and extrinsic hand muscle group, such as muscles in the thenar and hypothenar muscles, the interossei muscles originating between the metacarpal bones, the long flexors and extensors in the forearm, e.g. extensor pollicis longus muscle, extensor/flexor indicis muscle, or the like.

The input signals may be the results, or signature, of the recorded signal of a mathematical operation on the electrophysiological or non-electrophysiological measurements from the wearer of the prosthesis. For example, if the measurement is an EMG signal, the signature of the EMG may be the amplitude or the energy of the signal.

The mathematical signatures of the EMG signal in the time domain may be: amplitude (Mean absolute value of EMG and all its variations), energy (Square integral, Variance, Root means square (RMS)), number of zero crossing, Wilson amplitude, waveform length, slope sign change, or histogram of EMG.

The mathematical signatures of the EMG signal in the frequency domain may be: autoregressive and spectral coefficients or median and mean frequency.

The mathematical signatures of the EMG signal in the time-frequency may be: coefficients of the short time Fourier transform, or discrete or continuous wavelet coefficients.

The mathematical signatures of the EMG signal in higher order statistics may be: skewness or kurtosis of EMG or any other higher even-or-odd-order statistics, entropy or negentropy.

These signatures and others may be repeated for each of the input signals to the algorithm. Any combination of static and dynamic signature extraction may also be used.

It should also be appreciated that the above signatures may be extracted and a dimensionality reduction technique may be used, such as principal component analysis, to reduce to input dimensions to 2, 3, . . . etc.

The electronic device may include a predetermined operating profile of the prosthesis. The electronic device may include one or more predetermined operating profiles.

The or each, predetermined operating profile of the prosthesis may include an operating profile of the input command signal, operating mode of the moveable component and operating parameter(s) of the moveable component of the prosthesis.

The or each, predetermined operating profile of the prosthesis may be based on one or more input signals from the wearer of the prosthesis to produce an input command signal which results in selection of both the operating mode of the at least one moveable component and at least one operating parameter of the at least one moveable component.

The electronic device may be operable to modify the, or each, predetermined operating profile of the prosthesis to a modified operating profile. In this arrangement the electronic device may be operable to modify the, or each, predetermined operating profile to a new operating profile that the wearer of the prosthesis finds easier to operate. The modification of the, or each, predetermined operating profile may be reinforcement learning, iterative learning, co-adaptive control or the like.

The electronic device may be operable to switch between two or more predetermined operating profiles.

The or each, predetermined operating profile of the prosthesis may be based on one or more input signals from the wearer of the prosthesis to produce an input command signal which results in simultaneous selection of both the operating mode of the at least one moveable component and at least one operating parameter of the at least one moveable component.

The electronic device may be further operable to produce an output signal indicative of the operating mode of the at least one moveable component and/or the operating parameter of the at least one moveable component.

The electronic device may be further operable to produce an output signal indicative of the operating mode of the at least one moveable component and the operating parameters of the moveable component.

The electronic device may be further operable to communicate the output signal to the wearer of the prosthesis.

The output signal may be communicated to the wearer of the prosthesis visually, kinaesthetically, aurally or neurally.

The output signal may be communicated non-invasively to the wearer of the prosthesis via electro-tactile or vibro-tactile stimulation of the body skin. The electro-tactile or vibro-tactile stimulation to the body skin may be provided at the forearm, shoulder, neck, or the like.

The electronic device may be further operable to process the input command signal from the wearer of the prosthesis. The electronic device may be further operable to process the input signals from the wearer of the prosthesis.

The electronic device may be further operable to pre-process the input signals from the wearer of the prosthesis. The electronic device may be further operable to pre-process the input signals from the wearer of the prosthesis to predict the intended input command signal. The electronic device may be further operable to select both an operating mode of the at least one moveable component and at least one operating parameter of the at least one moveable component in response to the predicted input command signal.

The electronic device may include a processor. The processor may be operable to control the operation of the prosthesis. The processor may be operable to control the operation of the moveable component of the prosthesis. The processor may be operable to select both the operating mode of the at least one moveable component and at least one operating parameter of the at least one moveable component in response to the input command signal from the wearer of the prosthesis.

The electronic device may include firmware. The firmware may be operable to control the operation of the prosthesis. The firmware may be operable to control the operation of the moveable component of the prosthesis. The firmware may be operable to select both the operating mode of the at least one moveable component and at least one operating parameter of the at least one moveable component in response to the input command signal from the wearer of the prosthesis.

The processor may include the, or each, predetermined operating profile of the prosthesis.

The electronic device may be located with the prosthesis. The electronic device may be located with the wearer of the prosthesis.

According to a fourth aspect of the invention there is provided a method of operating a prosthesis having at least one moveable component, the at least one moveable component having two or more operating modes and at least one operating parameter, and an electronic device operable to control the operation of the at least one moveable component of the prosthesis, the method comprising the steps of:
providing the electronic device with an input command signal from the wearer of the prosthesis; and
using the electronic device to select both an operating mode of the at least one moveable component and at least one operating parameter of the at least one moveable component in response to the input command signal from the wearer of the prosthesis.

The moveable component may be a digit of a hand prosthesis. The digit may be a finger or a thumb of a hand prosthesis. The digits may be moveable relative to a body part to which they are attached. The digits may be rotatably and/or pivotably moveable relative to a body part to which they are attached. The body part may be attachable to the wearer of the prosthesis.

The prosthesis may be configured such that it is attachable to a partial-hand amputee. That is, the prosthesis may be arranged such that it is attachable to a wearer who is missing one or more fingers or a thumb from their hand, with the moveable components replacing the missing fingers or thumb.

The moveable component may be a body part to which a digit may be attached. The moveable component may be a hand chassis. The moveable component may be a wrist or cuff component. The body part or hand chassis may be rotatably attachable to the wearer of the prosthesis.

The term operating mode is considered here to mean an operating movement of the moveable component in response to an input command signal from the wearer of the prosthesis. When the prosthesis comprises two or more moveable components, the term operating mode is considered to mean the operational interaction between the moveable components in response to an input command signal from the wearer of the prosthesis.

Each operating mode provides for a discrete operating movement of the moveable component. When the prosthesis comprises two or more moveable components, each operating mode provides for a discrete operational interaction between the moveable components. The operational interaction between the moveable components may include functional tasks that the wearer of the prosthesis wishes the components to perform, such as pressing the components together in a pinching action, or moving the components to a desired position to create a gesture, such as pointing.

The term operating parameter is considered here to mean an operating condition of the moveable component in response to an input command signal from the wearer of the prosthesis. The operating parameter of the moveable component may include its speed, acceleration, deceleration, force, operating duration, amount of extension, amount of flexion, angle of rotation etc.

The operating parameter of the moveable component may be proportional to the input command signal. That is, the operating condition of the moveable component may be proportional to the input command signal.

The electronic device may be operable to select both the operating mode of the at least one moveable component and the operating parameters of the moveable components in response to an input command signal from the wearer of the prosthesis.

The electronic device may be operable to simultaneously select both the operating mode of the at least one moveable component and at least one operating parameter of the at least one moveable component in response to an input command signal from the wearer of the prosthesis.

The electronic device may be provided with a single input command signal from the wearer of the prosthesis.

The electronic device may be operable to select both the operating mode of the at least one moveable component and at least one operating parameter of the at least one moveable component in response to a single input command signal from the wearer of the prosthesis.

The at least one moveable component may have a plurality of operating modes.

The prosthesis may comprise a plurality of moveable components. Each moveable component may have two or more operating modes and at least one operating parameter.

Each moveable component may have a plurality of operating parameters.

The electronic device may be operable to select one of the plurality of operating modes of the at least one moveable component and at least one operating parameter of the at least one moveable component in response to an input command signal from the wearer of the prosthesis.

The electronic device may be operable to select one of the plurality of operating modes of the at least one moveable component and at least one operating parameter of the at least one moveable component in response to a predetermined input command signal from the wearer of the prosthesis.

Each predetermined input command signal may result in selection of a corresponding predetermined operating mode of the at least one moveable component and at least one operating parameter of the at least one moveable component.

The input command signal may comprise two or more input signals from the wearer of the prosthesis. The input command signal may comprise a plurality of input signals from the wearer of the prosthesis.

The input signals from the wearer of the prosthesis may be provided via one or more switches. The switches may be analogue or digital switches. The switches may be actuated by residual movement of the wearer of the prosthesis, wrist and/or shoulder movement of the wearer of the prosthesis, movement of the remnant digits and/or knuckles, or the like.

The input signals from the wearer of the prosthesis may be provided by electrophysiological signals derived from the activity of, or from, surface electromyographic (EMG) and intramuscular activity of residual muscle actions of the wearer of the prosthesis, electroneurographic (ENG) activity of residual peripheral nerves of the wearer of the prosthesis, signals derived from one or more neural implants in the wearer of the prosthesis implanted in the brain or spinal cord, EMG activity from re-innervated muscles, muscles of the feet and/or chest, or the like.

The input signals from the wearer of the prosthesis may be provided by non-electrophysiological signals derived from the activity of pressure sensitive resistors on the wearer of the prosthesis, near infrared spectroscopy signal, or bend sensitive resistors on the wearer of the body to capture any residual movement of the digits, wrist, elbow or shoulder of the wearer of the prosthesis, or the like.

The input signals from the wearer of the prosthesis may be provided directly by signals derived from neural, spinal or muscular activity, for example, electromyographic (EMG) activity of hand muscle/forearm muscle actions, or residual muscle actions, of the wearer of the prosthesis recorded non-invasively from the surface of the skin or invasively from superficial or deep muscular structures with using needle or an array of needle electrodes. The prosthesis may be controlled by the activity of any combination of intrinsic and extrinsic hand muscle group, such as muscles in the thenar and hypothenar muscles, the interossei muscles originating between the metacarpal bones, the long flexors and extensors in the forearm, e.g. extensor pollicis longus muscle, extensor/flexor indicis muscle, or the like.

The input signals may be the results, or signature of the recorded signal of a mathematical operation on the electrophysiological or non-electrophysiological measurements from the wearer of the prosthesis. For example, if the measurement is an EMG signal, the signature of the EMG may be the amplitude or the energy of the signal.

The mathematical signatures of the EMG signal in the time domain may be: amplitude (Mean absolute value of EMG and all its variations), energy (Square integral, Variance, Root means square (RMS)), number of zero crossing, Wilson amplitude, waveform length, slope sign change, or histogram of EMG.

The mathematical signatures of the EMG signal in the frequency domain may be: autoregressive and spectral coefficients or median and mean frequency.

The mathematical signatures of the EMG signal in the time-frequency may be: coefficients of the short time Fourier transform, or discrete or continuous wavelet coefficients.

The mathematical signatures of the EMG signal in higher order statistics may be: skewness or kurtosis of EMG or any other higher even-or-odd-order statistics, entropy or negentropy.

These signatures and others may be repeated for each of the input signals to the algorithm. Any combination of static and dynamic signature extraction may also be used.

It should also be appreciated that the above signatures may be extracted and a dimensionality reduction technique may be used, such as principal component analysis, to reduce to input dimensions to 2, 3, . . . etc.

The method may comprise the further step of providing the electronic device with a predetermined operating profile of the prosthesis. The method may comprise the further step of providing the electronic device with one or more predetermined operating profiles of the prosthesis.

The or each, predetermined operating profile of the prosthesis may include an operating profile of the input command signal, operating mode of the moveable component and operating parameter(s) of the moveable component of the prosthesis.

The or each, predetermined operating profile of the prosthesis may be based on one or more input signals from the wearer of the prosthesis to produce an input command signal which results in selection of both the operating mode of the at least one moveable component and at least one operating parameter of the at least one of the moveable component.

The electronic device may be operable to modify the, or each, predetermined operating profile of the prosthesis to a modified operating profile. In this arrangement the electronic device may be operable to modify the, or each, predetermined operating profile to a new operating profile that the wearer of the prosthesis finds easier to operate. The modification of the, or each, predetermined operating profile may be reinforcement learning, iterative learning, co-adaptive control or the like.

The electronic device may be operable to switch between two or more predetermined operating profiles.

The or each, predetermined operating profile of the prosthesis may be based on one or more input signals from the wearer of the prosthesis to produce an input command signal which results in simultaneous selection of both the operating mode of the at least one moveable component and at least one operating parameter of the at least one moveable component.

The electronic device may include a predetermined operating profile of the prosthesis. The predetermined operating profile of the prosthesis may include an operating profile of the input command signal, operating mode of the moveable component and operating parameter(s) of the moveable component of the prosthesis.

The predetermined operating profile of the prosthesis may be based on one or more input signals from the wearer of the prosthesis to produce an input command signal which results in selection of both the operating mode of the at least one moveable component and at least one operating parameter of the at least one moveable component.

The predetermined operating profile of the prosthesis may be based on one or more input signals from the wearer of the prosthesis to produce an input command signal which results in simultaneous selection of both the operating mode of the at least one moveable component and at least one operating parameter of the at least one moveable component.

The method may comprise the further step of using the electronic device to produce an output signal indicative of the operative mode of the at least one moveable component and/or the operating parameter of the at least one moveable component.

The electronic device may be further operable to produce an output signal indicative of the operative mode of the at least one moveable component and/or the operating parameter of the at least one moveable component.

The electronic device may be further operable to produce an output signal indicative of the operative mode of the at least one moveable component and the operating parameters of the moveable component.

The method of the invention may comprise the further step of communicating output signal to the wearer of the prosthesis.

The electronic device may be further operable to communicate the output signal to the wearer of the prosthesis.

The output signal may be communicated to the wearer of the prosthesis visually, kinaesthetically, aurally or neurally.

The output signal may be communicated non-invasively to the wearer of the prosthesis via electro-tactile or vibro-tactile stimulation of the body skin. The electro-tactile or vibro-tactile stimulation to the body skin may be provided at the forearm, shoulder, neck, or the like.

The method may comprise the further step of using the electronic device to process the input command signal from the wearer of the prosthesis. The method may comprise the further step of using the electronic device to process the input signals from the wearer of the prosthesis.

The electronic device may be further operable to process the input command signal from the wearer of the prosthesis. The electronic device may be further operable to process the input signals from the wearer of the prosthesis.

The method may comprise the further step of using the electronic device to pre-process the input signals from the wearer of the prosthesis. The method may comprise the further step of using the electronic device to pre-process the input signals from the wearer of the prosthesis to predict the intended input command signal. The method may comprise the further step of using the electronic device to select both an operating mode of the at least one moveable component and at least one operating parameter of the at least one moveable component in response to the predicted an input command signal.

The electronic device may be further operable to pre-process the input signals from the wearer of the prosthesis. The electronic device may be further operable to pre-process the input signals from the wearer of the prosthesis to predict the intended input command signal. The electronic device may be further operable to select both an operating mode of the at least one moveable component and at least one operating parameter of the at least one moveable component in response to the predicted an input command signal.

The electronic device may include a processor. The processor may be operable to control the operation of the prosthesis. The processor may be operable to control the operation of the moveable component of the prosthesis. The processor may be operable to select both the operating mode of the at least one moveable component and at least one operating parameter of the at least one moveable component in response to the input command signal from the wearer of the prosthesis.

The electronic device may include firmware. The firmware may be operable to control the operation of the prosthesis. The firmware may be operable to control the operation of the moveable components of the prosthesis. The firmware may be operable to select both the operating mode of the at least one moveable component and at least one operating parameter of the at least one moveable component in response to the input command signal from the wearer of the prosthesis.

The processor may include the, or each, predetermined operating profile of the prosthesis.

The electronic device may be located with the prosthesis. The electronic device may be located with the wearer of the prosthesis.

An embodiment of the invention will now be described, by way of example only, with reference to the accompanying drawings, in which:—

Figure 1:
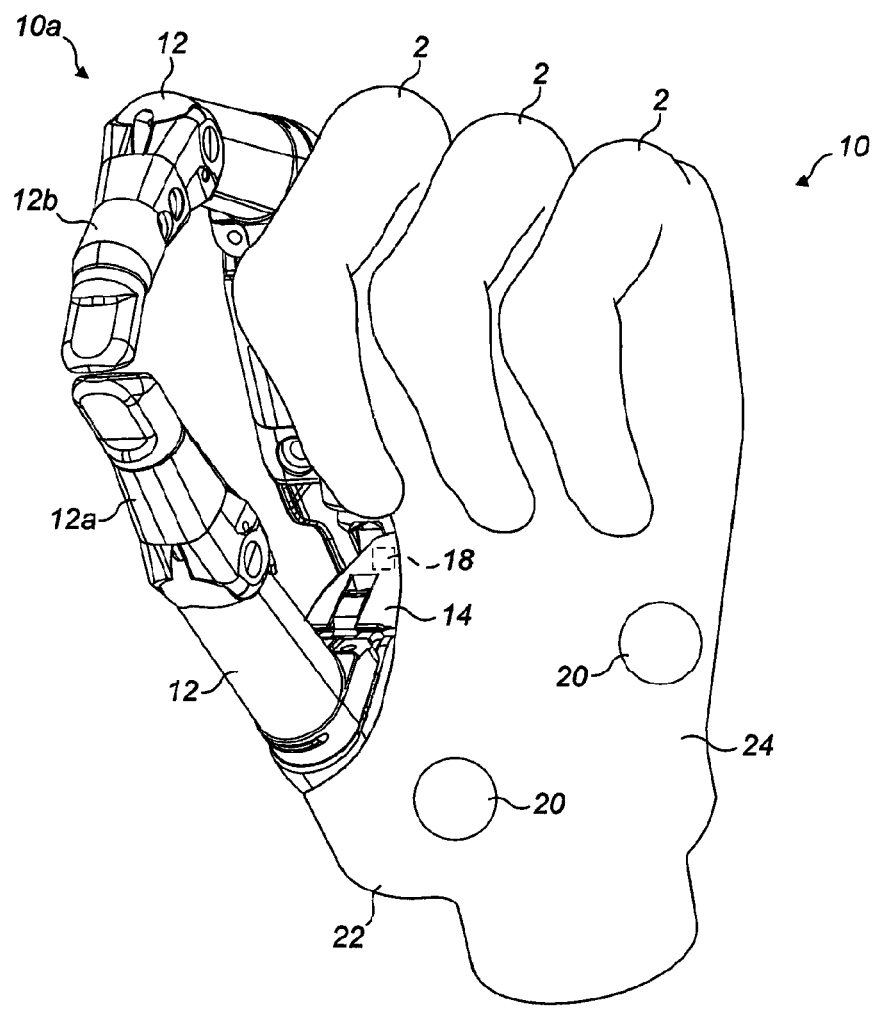
FIG. 1 illustrates a prosthesis according to the present invention fitted to a partial-hand amputee.

FIGS. 1 to 8 illustrate a prosthesis 10 according to the present invention. FIG. 1 illustrates a prosthesis 10*a* of the present invention fitted to a hand 1 of a partial-hand amputee. FIGS. 2 to 8 illustrate the prosthesis 10*b* of the present invention in a "full hand" configuration, which replaces the entire hand of an amputee.

With reference to FIG. 1, the prosthesis 10*a* is fitted to a partial-hand amputee that is missing their thumb and forefinger. The remaining fingers have the reference number 2. The prosthesis 10*a* comprises two moveable digits 12 (thumb 12*a* and forefinger 12*b*), which are examples of moveable components. The digits 12 are attached to a body part 14 (hand chassis). The body part 14 is attachable to the limb of the amputee in a known manner. The digits 12 are arranged such that they can rotate and/or pivot with respect to the body part 14. The digits 12 are powered digits, such as those disclosed in WO 2007/063266 and WO 1995/24875. The digits 12 are therefore mechanically operated digit members that are moved by an electric motor.

With reference to FIGS. 2 to 8, the "full hand" prosthesis 10b comprises a body part 14 and five digits 12 (a thumb 12a and four fingers 12b). The body part 14 is rotatably attached to an attachment component 16, which is used to attach the prosthesis 10b to the wearer. In this arrangement the prosthesis 10b is a replacement for the entire hand of the amputee.

Figure 8:
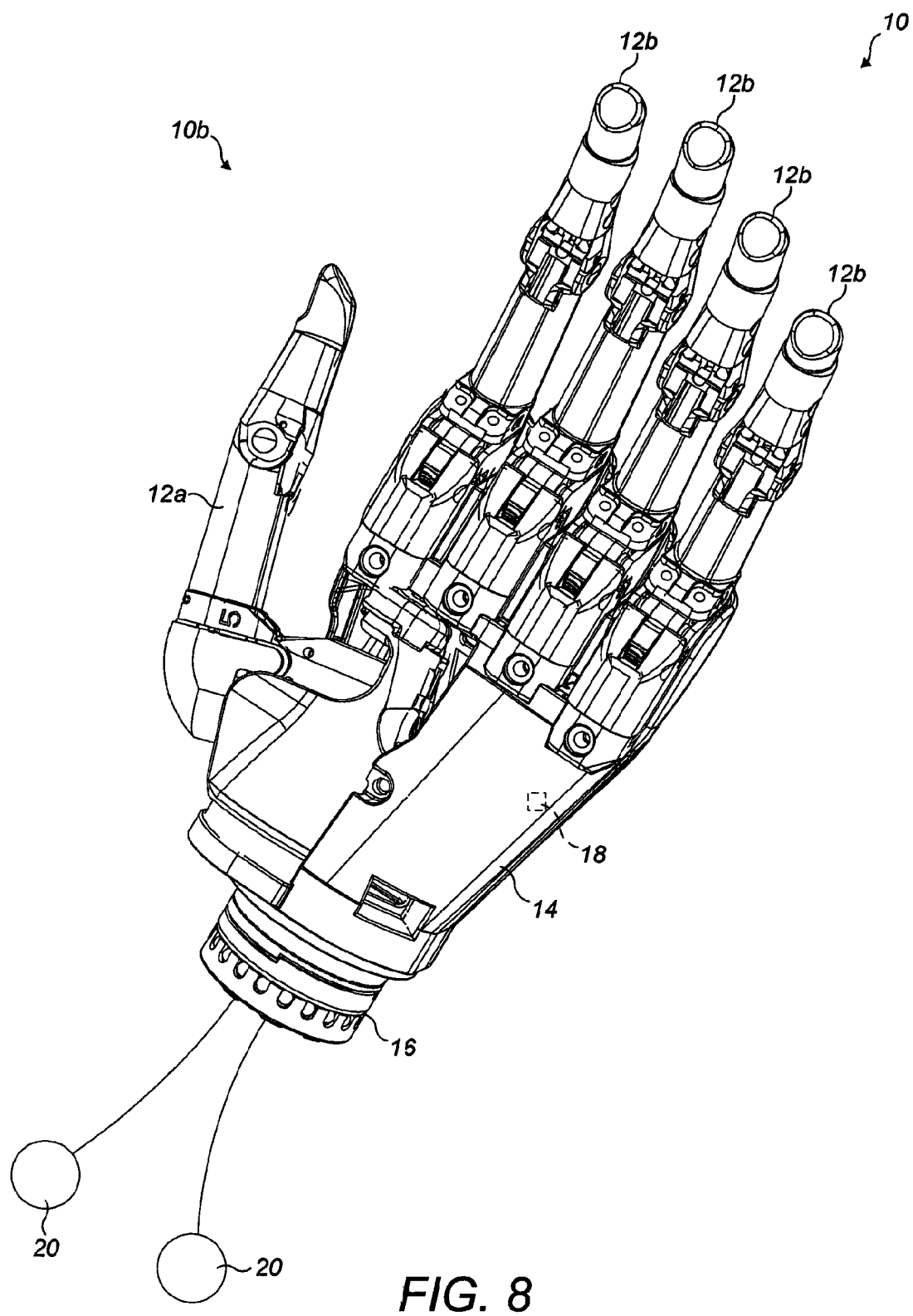

As illustrated in FIGS. 1 to 8 and explained below, the finger digits 12b may pivot with respect to the body part 14 and, as is known in the art, flex and extend in the same manner as a human finger. In addition to flexing and extending, the thumb digit 12a may also pivot with respect to the body part 14, as illustrated in FIG. 8 and explained further below. It should also be appreciated that the body part 14 itself may be a moveable component. For example, in the case of the "full hand" prosthesis 10b of FIGS. 2 to 8, the body part 14 may rotate relative to the attachment component 16, which is fitted to the wearer of the prosthesis. The body part 14 may be motor driven with respect to the attachment component 16. In this case, the body part 14 can perform the function of "wrist rotation" in the same manner as a human hand.

As described above and as illustrated in FIGS. 1 to 8, the digits 12 of the prosthesis 10a, 10b are moveable with respect to the body part 14 such that the prosthesis 10a, 10b may provide a plurality of hand configurations, gestures and operations that are similar to those performed by a healthy human hand.

Figure 2:
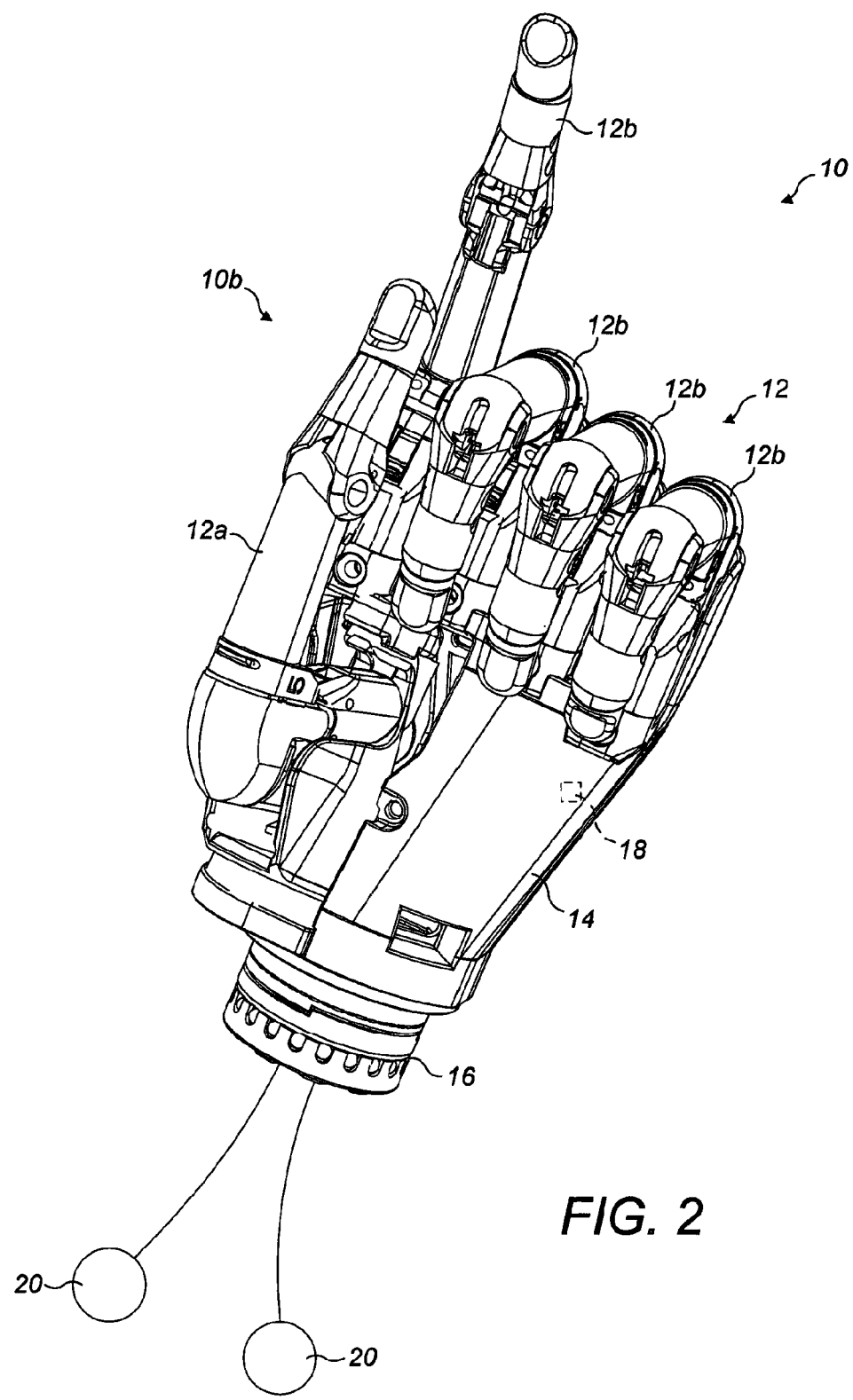
FIGS. 2 to 8 illustrate a "full hand" prosthesis according to the present invention in a number of operating modes.
Figure 3:
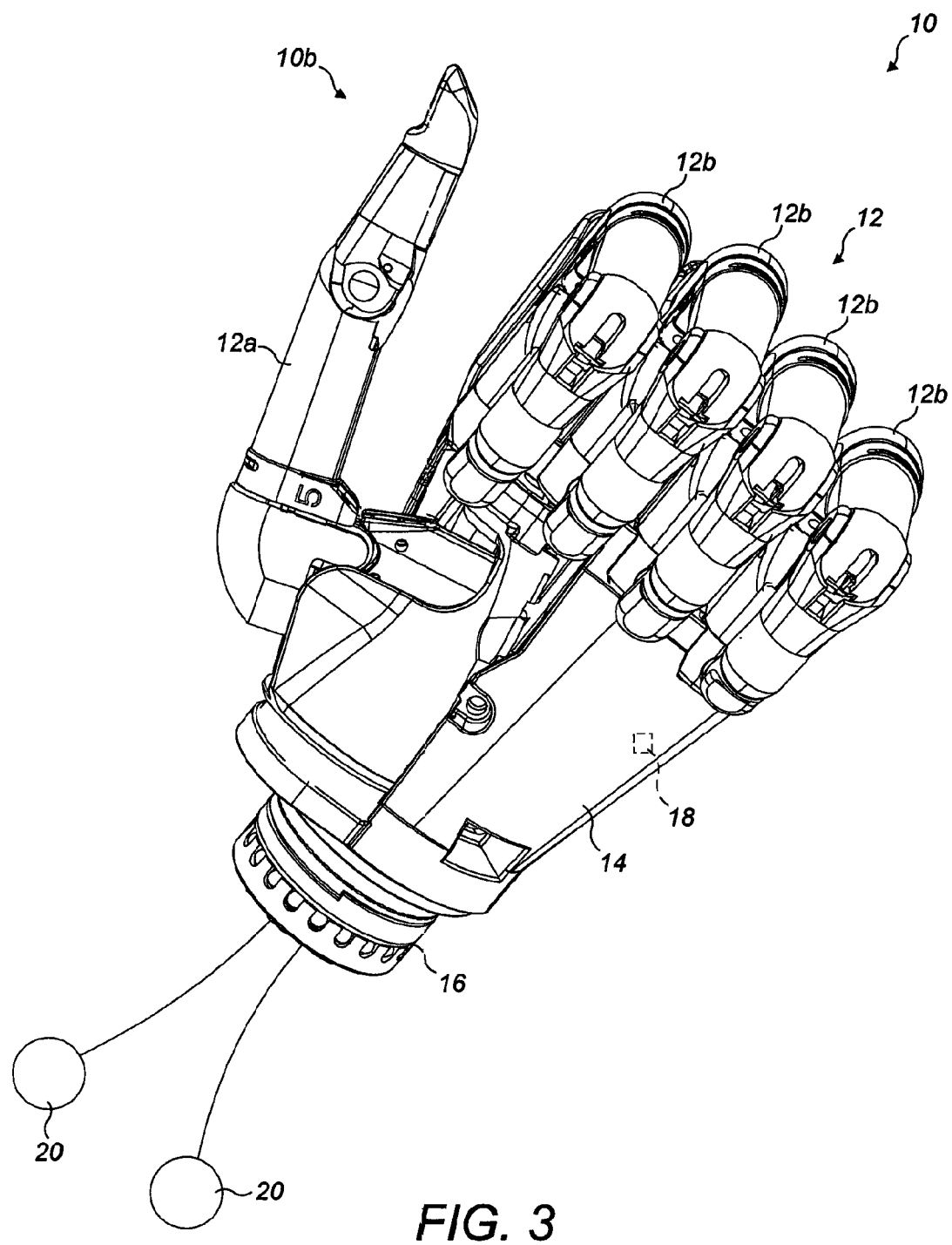
Figure 4:
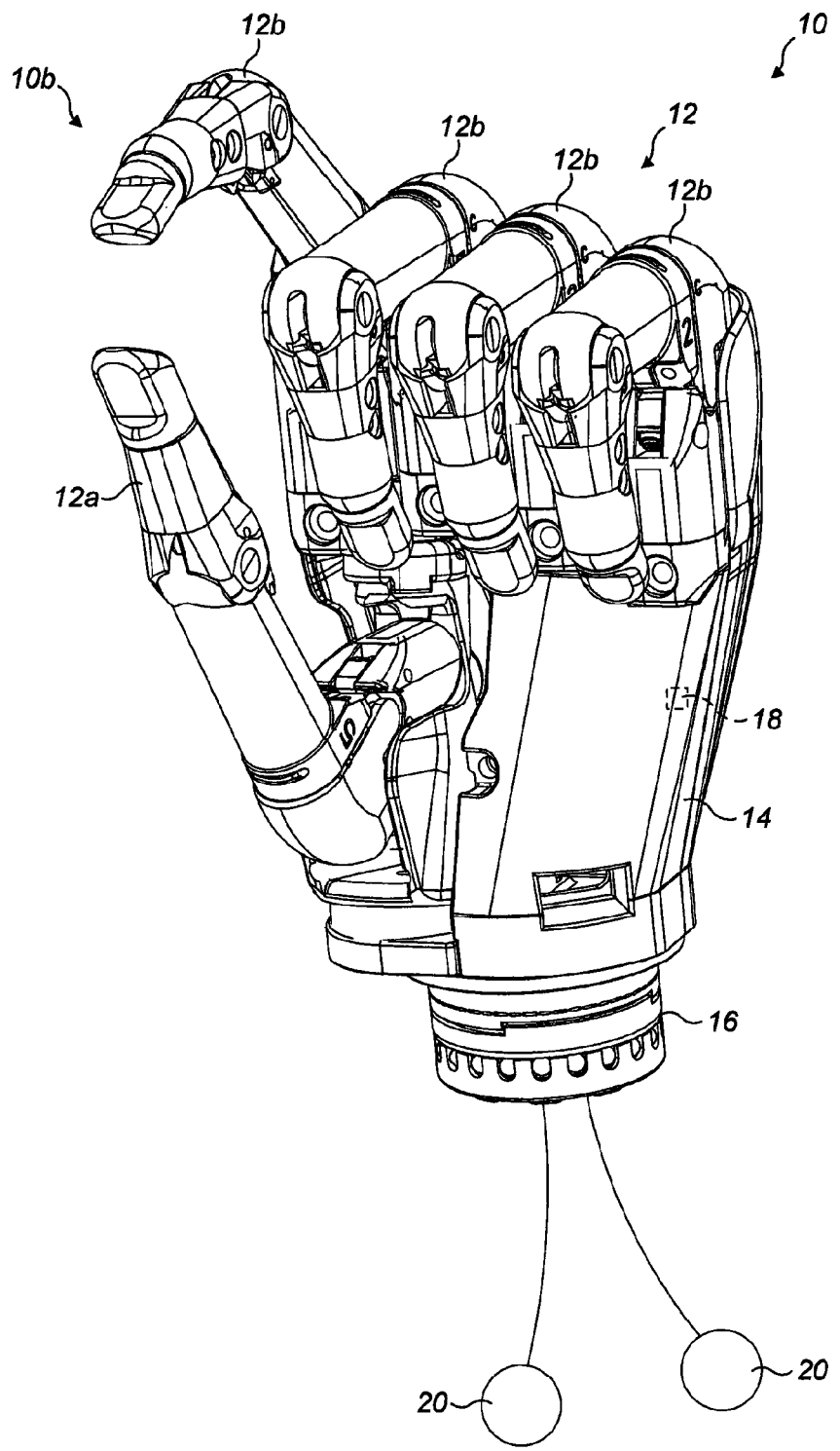
Figure 5:
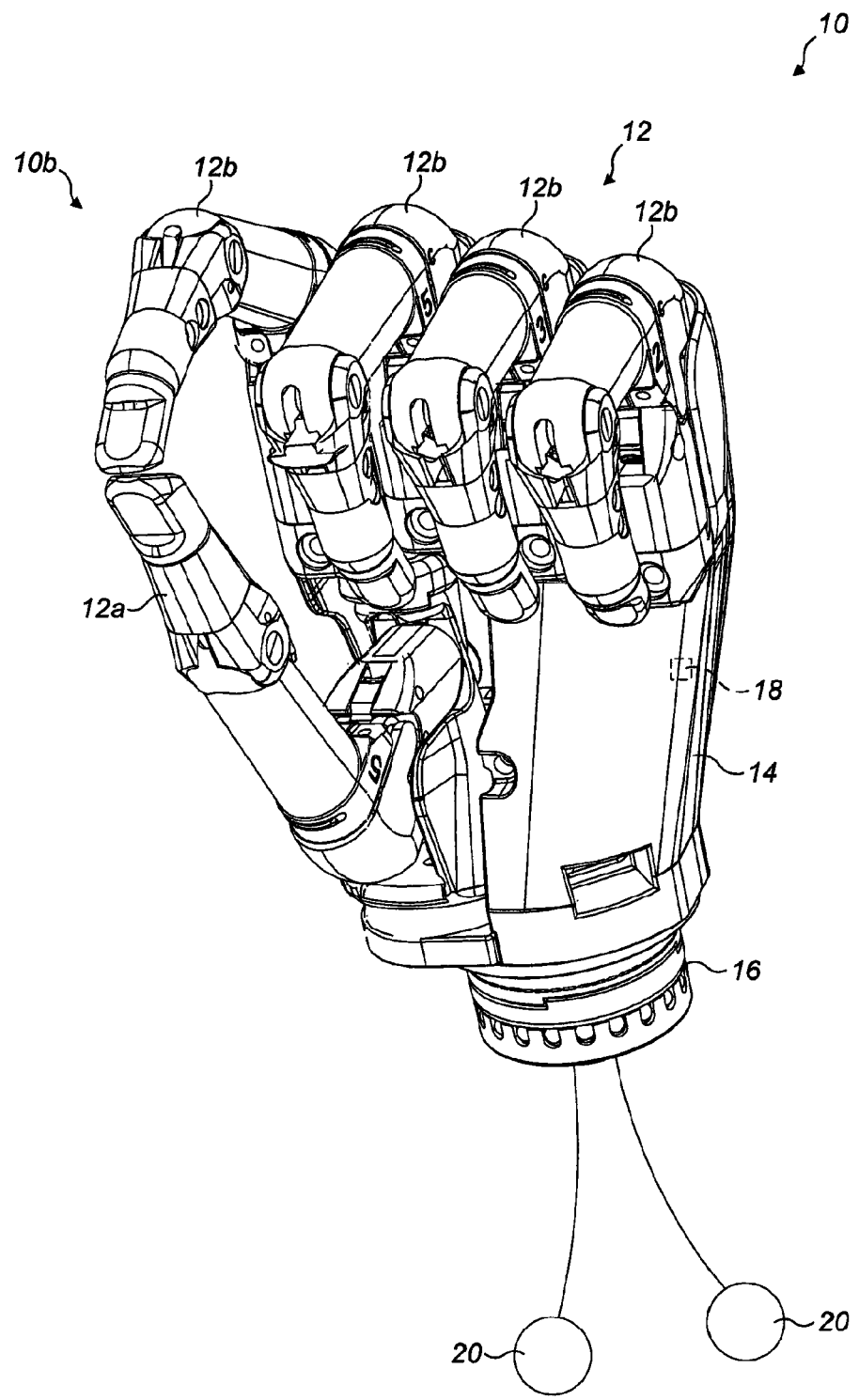
Figure 6:
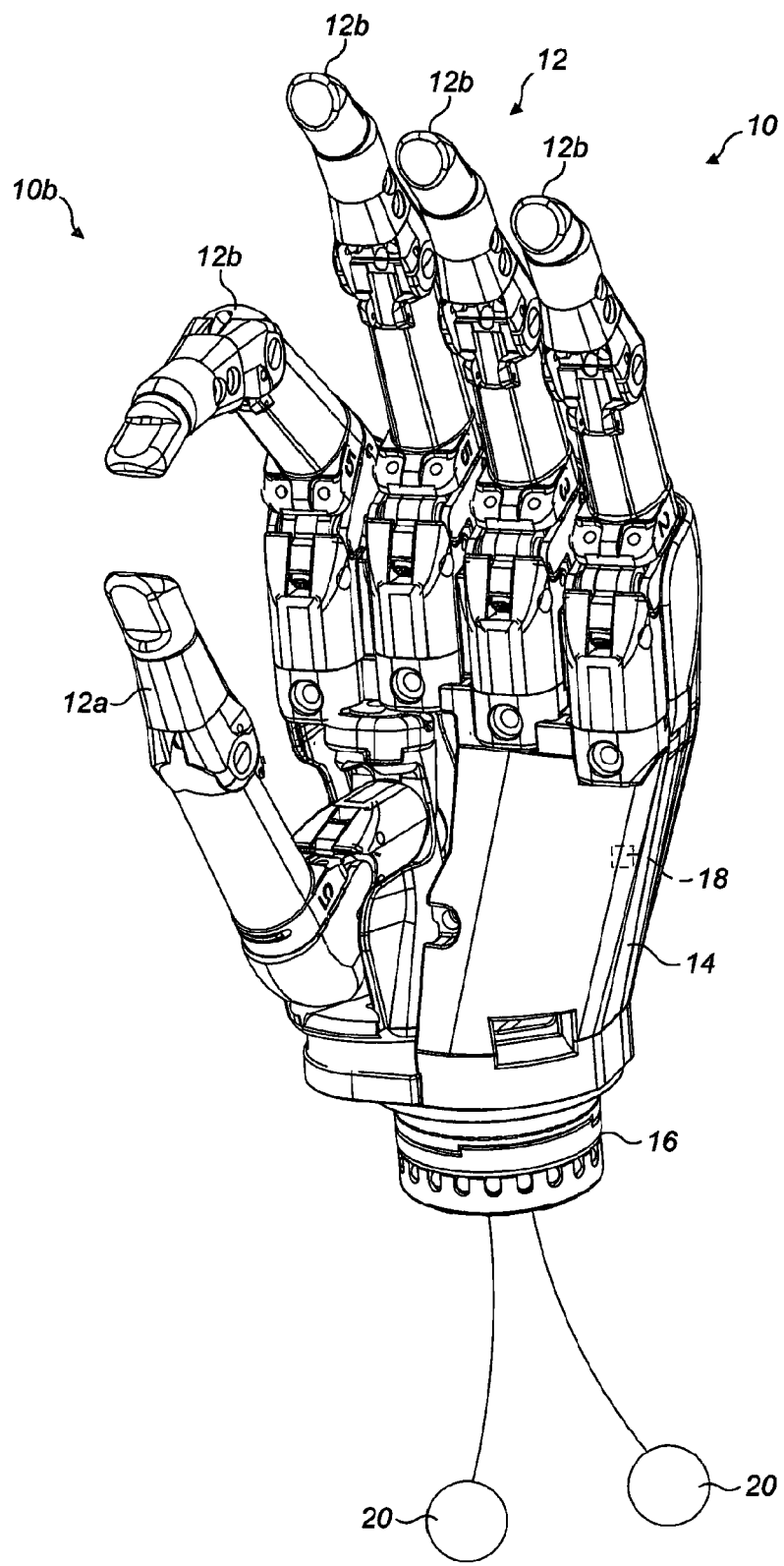
Figure 7:
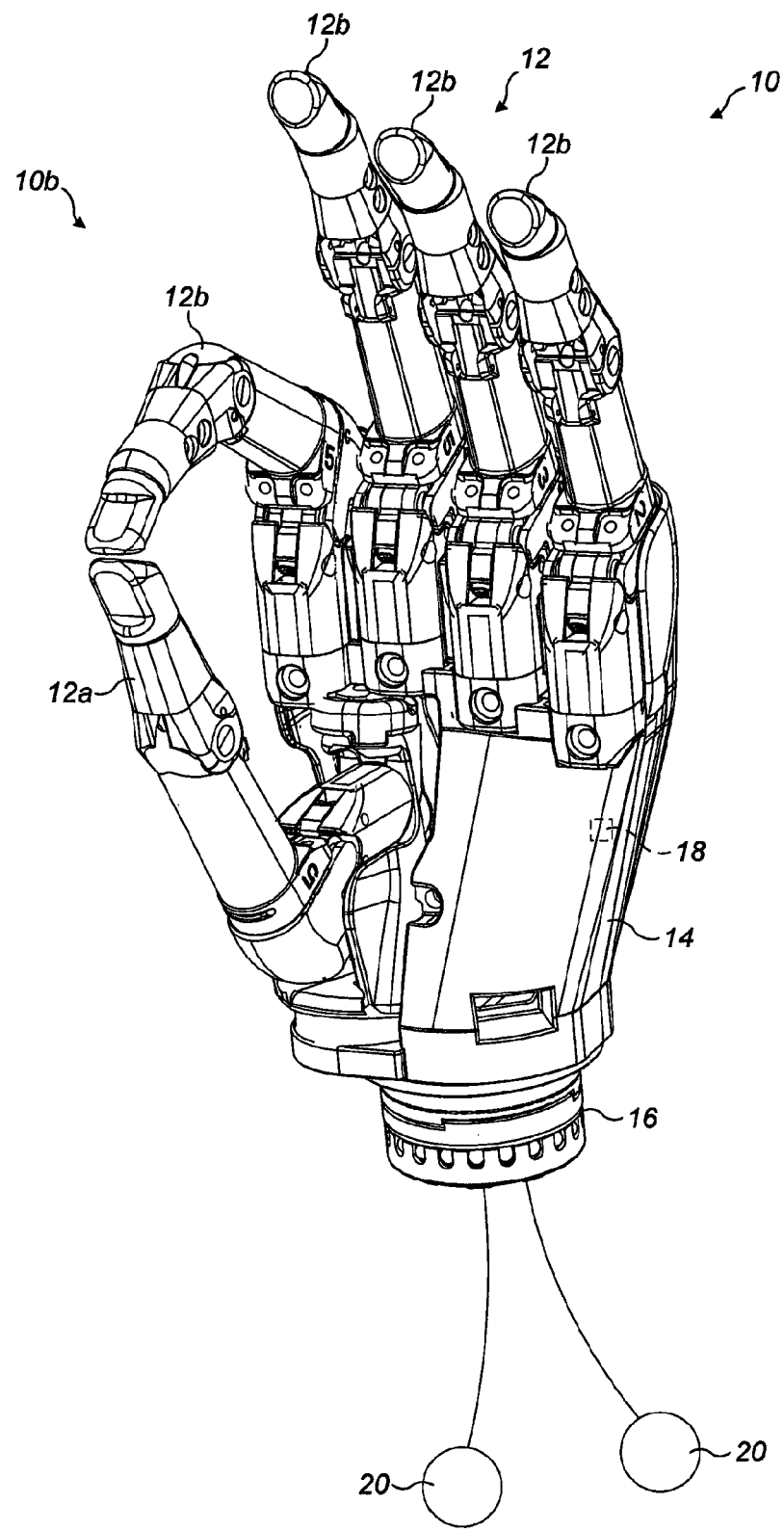

FIGS. 1 and 4 to 7 illustrate configurations of the prosthesis 10a, 10b operating in "pinch" mode, i.e. where the prosthesis 10a, 10b is operated to bring thumb digit 12a and the forefinger digit 12b into and out of contact with one another. FIG. 2 illustrates a "pointing" gesture, where the forefinger digit 12b is extended and the other finger digits 12b are "closed". FIG. 3 illustrates a "grasp" configuration, where the prosthesis 10b would be used to hold an object. FIG. 8 illustrates a "waving" gesture, where the digits 12 are extended and the thumb digit 12a is rotated away from the body part 14. The rotation of the entire thumb digit 12a relative to the body part 14 can be seen from a comparison of FIGS. 1 and 2, for example. Again, it should be noted that the body part 14 of FIGS. 2 to 8 may rotate relative to the attachment component 16.

The configurations and gestures illustrated in FIGS. 1 to 8 may be considered to be the operating modes of the digits 12 of the prosthesis 10a, 10b. The rotation of the body part 14 relative to the attachment component 16 may also be considered as an operating mode of the body part 14 of the prosthesis 10b. The direction of rotation of the body part 14 may be considered as an operating mode thereof. The prosthesis 10a, 10b may thus be considered as having a plurality of operating modes. The operating modes are selected by the wearer of the prosthesis 10a, 10b depending on the operation they wish the prosthesis 10a, 10b to perform.

The digits 12 of the prosthesis 10a, 10b also have a number of operating parameters. That is, the digits 12 have a number of operating conditions, such as their speed of movement, acceleration, deceleration, applied force, operating duration, amount of extension, amount of flexion and angle of rotation. The body part 14 also includes a number of operating conditions, such as its speed of movement, acceleration, deceleration, applied force, operating duration and angle of rotation. The prosthesis 10a, 10b may thus be considered as having a plurality of operating parameters. The operating parameters are selected by the wearer of the prosthesis 10a, 10b depending on the operation they wish the prosthesis 10a, 10b to perform.

The prosthesis 10a, 10b also comprises an electronic device 18 which controls the operation of the digits 12 (and body part 14 for the "full hand" prosthesis 10b). The electronic device 18 includes a processor and firmware (not shown) which together control the operation of the digits 12.

The electronic device 18 may be located within the body part 14, or alternatively be located on the wearer of the prosthesis 10a, 10b.

The electronic device 18 controls the operation of the digits 12 in response to one or more input control signals from the wearer. In the embodiments illustrated and described here the input control signals are derived from electrophysiological signals derived from the activity of, or from, surface electromyographic (EMG) or intramuscular activity of residual muscle actions of the wearer of the prosthesis.

For the "partial-hand" prosthesis 10a illustrated in FIG. 1, the input control signals come from two electromyographic (EMG) sensors 20 located, for example, on the thenar muscle group 22 and the hypothenar muscle group 24. For the "full hand" prosthesis 10b illustrated in FIGS. 2 to 8, the input control signals come from two electromyographic (EMG) sensors (not shown) located on, for example, the muscle groups of the arm of the wearer. The electrophysiological signals produced from the residual muscles to which the EMG sensors 20 are attached are proportional to the activity of the muscles. Thus, the input control signals from the EMG sensors 20 allow proportional control of the digits 12 of the prosthesis 10a, 10b. For example, this allows the wearer to proportionally control the speed of the operation of the digits 12.

It should be appreciated that any number of input signals and EMG sensors 20 could be used to control the operation of the digits 12 of the prosthesis.

The electronic device 18 is operable to select both an operating mode of the digits 12 and at least one operating parameter of the digits 12 in response to an input command signal from the wearer of the prosthesis 10a, 10b. For example, the electronic device 18 is operable to select the "pinch" mode of FIG. 4 with a slow speed of movement and low pinch force of the digits 12 in response to a single input command signal from the wearer. Such an operation of the prosthesis 10b may be desired by the wearer when, for example, they wish to pick up a delicate object.

The electronic device 18 processes the input control signals from the EMG sensors 20 and produces the input command signal to control the digits 12. It is important to note that the input command signal is a single signal which selects both the operating mode and the operating parameter(s) of the digits 12 of the prosthesis 10a, 10b.

Figure 9:
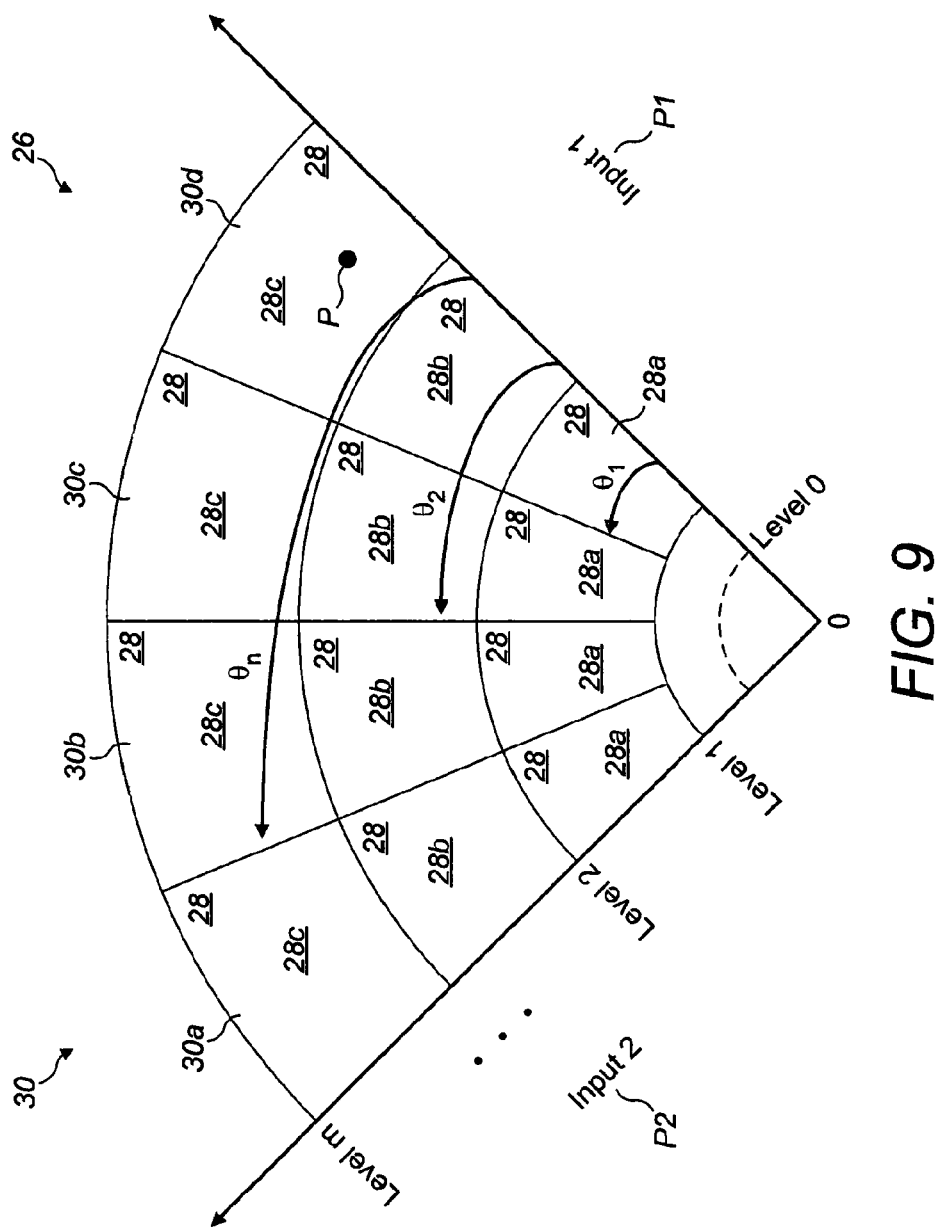
FIG. 9 is an illustrative example of a predetermined operating profile of the prosthesis with two input control signals.
Figure 10:
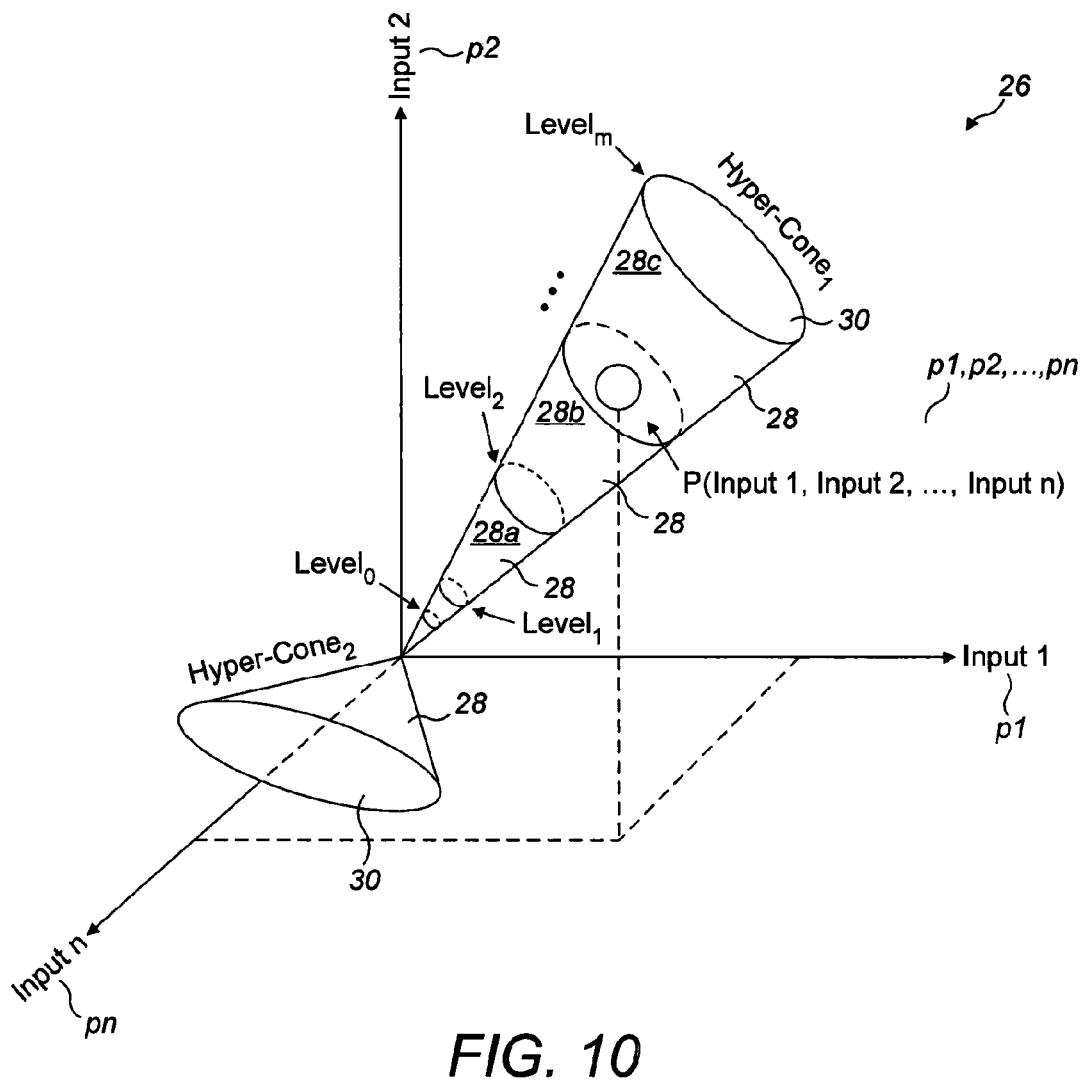
FIG. 10 is an illustrative example of a predetermined operating profile of the prosthesis with n input control signals.

The electronic device 18 includes a predetermined operating profile 26 of the prosthesis 10a, 10b. An example predetermined operating profile 26 of the prosthesis 10a, 10b is illustrated in FIGS. 9 and 10. The predetermined operating profile 26 provides for determination of the input command signal for the electronic device 18 in response to the input control signals from the EMG sensors 20 on the wearer of the prosthesis 10a, 10b.

FIG. 9 illustrates the predetermined operating profile of a prosthesis with two input signals and FIG. 10 illustrates the predetermined operating profile of a prosthesis with n input signals. FIG. 10 is essentially a n dimensional version of the predetermined operating profile of FIG. 9.

With reference to FIG. 9, the predetermined operating profile 26 provides an input command signal P for the electronic device 18 in response to two input control signals p1, p2 from the EMG sensors 20 on the wearer. As illustrated, the operating profile 26 is arranged into a number of areas 28. Each area 28 represents an operating mode and operating parameter of the digits 12 of the prosthesis 10a, 10b. Therefore, the input control signals p1, p2 from the EMG sensors 20 on the wearer determine which area 28 the point P lies, which, in turn, determines the input command signal P for the electronic device 18.

In the embodiment illustrated in FIG. 9 and described here, the operating profile 26 includes four segments 30a to 30d. Each segment 30a to 30d represents a different operating mode of the digits 12 of the prosthesis 10a, 10b and each area 28a to 28c represents a value or magnitude of an operating parameter of the digits 12 of the prosthesis 10a, 10b. Level 1 to m indicates, for example, the value or magnitude of the input control signals p1, p2. For example, segment 30a could represent the "pinch" mode (FIGS. 4 and 5) of the digits 12 and area 28a thereof could represent a minimum applied force of the digits 12, i.e. a strong pinch. In another example, segment 30d could represent the "point" gesture mode (FIG. 2) of the digits 12 and the area 28c thereof could represent the speed of extension of the forefinger digit 12b. However, it should be appreciated that the operating profile 26 is configurable to meet the needs, demands and/or abilities of the wearer of the prosthesis 10a, 10b. For example, the operating profile 26 may include any number of segments 30 and areas 28 therein. The number of segments 30 may be selected by the wearer depending on how many operating modes they wish to use. The number of segments 30 may only be limited by the number of operating modes that the digits 12 have. Similarly, the number of areas 28 in the segments 30 may be chosen by the wearer depending on the number of options they wish to control the operating parameter(s) of the digits 12.

With reference to FIG. 10, the use of two or more input control signals p1, p2, pn, dramatically increases the number of segments 30 and areas 28 available to the wearer of the prosthesis 10a, 10b. Each segment 30 and area 28 is again representative of a different operating mode of the digits 12 of the prosthesis 10a, 10b and a value or magnitude of an operating parameter of the digits 12 of the prosthesis 10a, 10b. Using more input control signals dramatically increases the control options and level of control offered to the wearer of the prosthesis 10a, 10b. Again, it should be appreciated that the operating profile 26 is configurable to meet the demands and/or abilities of the wearer of the prosthesis 10a, 10b.

As described above, it is important to note that the operating profile 26 is entirely configurable to meet the demands and abilities of the wearer. That is, it is not essential that the areas 28 of the operating profile 26 be arranged in any particular sequence or order, such as those illustrated and described above with reference to FIGS. 8 and 9. It is, however, important that any given area 28 is representative of a chosen operating mode and operating parameter(s) selected by the wearer of the prosthesis 10a, 10b, and that the wearer of the prosthesis 10a, 10b knows the input signals p1, p2, etc. required to obtain the input command signal P for the electronic device 18 to control the digits 12.

It is also important to note that the boundaries and the size of the areas 28 may be configured depending on the needs, demands and abilities of the wearer, or by the wearer, clinician or intelligently by the electronic control device 18.

As described above, the electronic device 18 includes the predetermined operating profile 26. The predetermined operating profile 26 is, for example, stored in the firmware of the electronic device 18. The electronic device 18 processes the input control signals p1, p2, . . . , pn, from the EMG sensors 20 on the wearer and determines the input command signal P from the operating profile 26. The electronic device 18 then uses this input command signal P to control the operation of the digits 12 of the prosthesis 10a, 10b in the manner desired by the wearer. As described above, the input command signal P is a single signal which results in selection of both the operating mode of the digits 12 of the prosthesis 10a, 10b and the operating parameters(s) of the digits 12 of the prosthesis 10a, 10b.

The electronic device 18 is also capable of pre-processing the input signals p1, p2, etc. to predict the intended input command signal P from the wearer of the prosthesis 10a, 10b. The pre-processing and prediction of the intended input command signal P is carried out by the firmware and processor of the electronic device 18. The electronic device 18 is then capable of selecting both the operating mode of the digits 12 and the operating parameter(s) of the digits 12 on the basis of the predicted input command signal P'. This function is useful where the wearer of the prosthesis 10a, 10b repeats the same action on a regular basis. It also reduces the time taken select the operating mode of the digits 12 and the operating parameter(s) of the digits 12. This "predictive" function can be switched on and off by the wearer as required.

Figure 11:
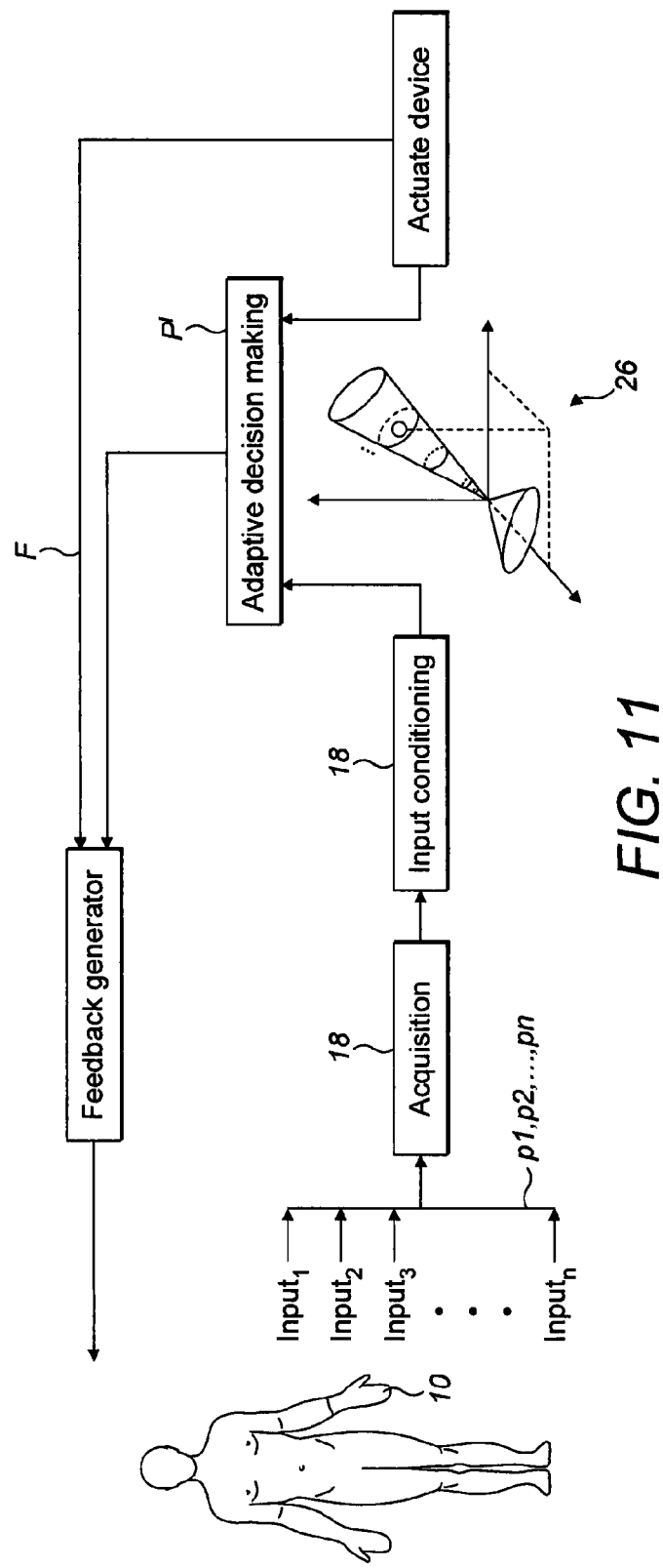
FIG. 11 is a schematic diagram illustrating the operation of the prosthesis.

The electronic device 18 is also capable of producing a feedback signal F to the wearer of the prosthesis 10a, 10b which is indicative of the operating mode of the digits 12 and the operating parameter(s) of the digits 12 (see FIG. 11). The feedback signal F is an signal output by the electronic device 18 which may be communicated to the wearer visually, kinaesthetically, aurally or neurally. The feedback signal F may be communicated non-invasively to the wearer of the prosthesis via electro-tactile or vibro-tactile stimulation of the body skin. The electro-tactile or vibro-tactile stimulation to the body skin may be provided at the forearm, shoulder, neck, or the like. This function is useful when, for example, the wearer cannot see the prosthesis 10a, 10b and cannot visually check that the intended operation is being carried out, i.e. that the input command signal is correct.

The prosthesis 10a, 10b may include a plurality of predetermined operating profiles 26. Each predetermined operating profile 26 may have its own arrangement of boundaries and size of the areas 28, depending on the needs, demands and abilities of the wearer, clinician or intelligently by the electronic control device 18.

The electronic device 18 is also capable of selecting a predetermined operating profile 26 from the plurality of predetermined operating profiles 26 that may be available. The electronic device 18 is also capable of switching between two predetermined operating profiles 26.

The ability to switch between two, or more, predetermined operating profiles 26 may be useful if the wearer of the prosthesis 10a, 10b becomes fatigued. The electronic device 18 may therefore be configured to switch between a "normal" mode (a first predetermined operating profile) and a "fatigue" mode (a second predetermined operating profile) . The switch between the two modes may be decided by the wearer of the prosthesis 10a, 10b, or automatically decided by the electronic device 18. If the switch between the two modes is decided by the wearer, the prosthesis 10a, 10b may be provided with a mechanical switch, or the like, to effect the selection of the desired predetermined operating profile 26. If the switch between the two modes is decided by the electronic device 18, the electronic device 18 may be provided with software to effect the selection of the desired predetermined operating profile 26.

In this arrangement the prosthesis 10a, 10b is configured such that it can measure the wearer's muscle fatigue. Fatigue measurement can be via monitoring the power spectrum of the electromyogram signal in time or in the frequency domain, e.g. a decrease in median power frequency can show increase in fatigue.

Detection of the onset of fatigue can be via many approaches, such as (i) if the signature of fatigue crosses a threshold, (ii) via supervised and unsupervised pattern recognition, such as neural networks, dimensionality reduction or clustering techniques and (iii) predictive control and time series nowcasting and forecasting.

The process of adjusting for fatigue can be either via recalibration by a clinician, or intelligently by an adaptive algorithm that can re-tune the predetermined operating profile 26.

Fatigue can cause change in two parameters (or both) in the control system: (i) involuntary co-contraction of muscles that control the hand (In this case in FIG. 9, boundaries of 30a, 30b, 30c and 30d will be adjusted (manually or intelligently) to minimise the effect of fatigue.) and (ii) reduction in the amplitude of the EMG (In this case in FIG. 9, margins 28a, 28b, 28c and 28d and level 0 will be adjusted (manually or intelligently) to minimize the effect of fatigue.)

With reference to FIG. 11, the operation of the prosthesis 10a, 10b will now be described. As described above, before the prosthesis 10a, 10b can be used by the wearer it is necessary to create an operating profile 26 for the wearer. While it is possible for the wearer to be provided with an existing operating profile, it is likely that the wearer will wish to create their own operating profile 26, which, as described above, is based on their needs, abilities and available input control signal options.

An important part of the creation of the operating profile 26 is the wearer learning to use muscle groups, such as the thenar and hypothenar muscle groups, to produce the input command signal P. This activity involves the wearer using muscle groups (and potentially other input signal functions) which are non-intuitive to the wearer, i.e. there is no "intuitive" link between the input control signal and the desired function of the prosthesis 10a, 10b. That is, the movement of the digit(s) 12 can be initiated and controlled by, for example, a muscle (or a combination of n muscle activity) that does not necessarily control the function of that digit(s) before amputation, i.e. in healthy and able-bodied condition. For example, the thumb muscle can control the movement of the little finger or the wrist. However, after a period of training and learning to create and control the input signals p1, p2 etc. an operating profile 26 is created which the wearer is comfortable with and can easily use.

With reference to FIGS. 9 and 10, an example of the operational control of the prosthesis 10a, 10b will now be described. When a wearer of the prosthesis 10a, 10b is learning how to use the prosthesis 10a, 10b and how to configure their operating profile 26, the operating profile 26 may be displayed on a computer screen in real time with the input control signals p1, p2, ..., pn producing the input command signal P on the operating profile 26. The input command signal P in this example may be considered as a cursor, which is moved around the operating profile 26 in dependence on the input control signals p1, p2, ..., pn from the wearer.

In a rest position, i.e. where there is no input control signals p1, p2, ..., pn from the wearer, the cursor is located at the origin O. To trigger the creation of an input command signal P the cursor should remain in an area 28 for a predetermined period. This period may be of the order of t milliseconds. With reference to FIG. 9, if the cursor is moved to, for example, area 28c, and stays there for less than t milliseconds, then quickly moves to an adjacent area 28c, and remains there for t milliseconds, then two predetermined operations are triggered one after the other. In order to avoid such rapid selection of predetermined operations, t may be set to, for example, 200 milliseconds. The value of the period t may be selected on the requirements of the wearer.

In known prostheses, if a mode of operation is triggered by EMG activity, the hand stays in that mode until the wearer changes the mode by producing, for example, some other muscle activity. In the present invention the prosthesis 10a, 10b may be operated as follows: if the segment 30d, for example, is associated with a "pinch" function and the wearer initiates a pinch function, in order to keep the pinch, the wearer should continue to produce input control signals p1, p2, ..., pn in the same way to keep the cursor (input command signal P) in the same area 28 of the segment 30. As soon as the wearer relaxes the controlling muscles, the cursor goes back to the origin O.

The predetermined operating profile 26 may have an absolute activity threshold (Level 0) and the prosthesis 10a, 10b may have two operational conditions. In the first operation condition the operating profile 26 may have an absolute activity threshold, i.e. there is a level 0. If the input control signals p1, p2, ..., pn are such that the cursor is below the level 0 the whole hand electronics shuts off to save energy. The microprocessors of the electronic device 18 wake up every x milliseconds to check the status. If the input control signals p1, p2, ..., pn are such that the cursor is still below the level 0, the electronics remain switched off. If the input control signals p1, p2, ..., pn are such that the cursor is above the level 0, the cursor is moved to this position.

The gap between the level 0 position and the level 1 position is also considered as an area 28, as described above, and results in the selection of both an operating mode and operating parameter(s) of the digits 12. This operating mode and operating parameter(s) may be, for example, a "hand open" configuration, a "thumb park" configuration, or a "predetermined natural hand configuration". If the input control signals p1, p2, ..., pn are such that the cursor goes through the gap between the level 0 and level 1 zones and stays there for t>200 milliseconds, the operating mode and operating parameter(s) are selected in the same manner as described above for areas 28.

If the input control signals p1, p2, ..., pn are such that the cursor goes through the gap between the level 0 and level 1 zones and stays there for t<200 milliseconds and then travels to the area below level 0, the electronic device 18 shuts off and the prosthesis 10a, 10b is maintained in the last configuration (i.e. operating mode and parameter(s)).

To open the hand, or to go to any other relax mode of operation, e.g. natural rest, the wearer may again take the cursor to the gap area between level 0 and level 1.

In the second operation condition the operating profile 26 may not have an absolute activity threshold, i.e. there is no level 0. In this arrangement the gap between the origin O and level 1 commands a predetermined operating mode and operating parameter(s) of the prosthesis 10a, 10b, e.g. "hand open", "thumb park", or a "predetermined natural hand configuration", i.e. relax mode. In this arrangement the electronic device 18 may still power down the electronics, as above.

The only difference between the first and second operating conditions is that in the second operating condition the hand does not keep the last gesture (operating mode and parameter(s)) when there are no input control signals p1, p2, . . . , pn, it opens regardless.

As illustrated in FIG. 11, input control signals p1, p2, . . . , pn are provided from the EMG sensors 20 on the wearer. The electronic device 18 acquires and processes the input control signals p1, p2, . . . , pn. The processing may include some signal processing, filtering etc., as is known in the art. The electronic device 18 then uses the operating profile 26 to determine the input command signal P from the input control signals p1, p2, . . . , pn. Once the input command signal P has been determined the electronic device 18 controls the digits 12 in the desired manner. That is, the electronic device 18 selects both the operating mode of the digits 12 and the operating parameter(s) of the digits 12 in dependence of the input command signal P. Note: the electronic device 18 may be set to predict the intended input command signal P from the wearer. If this is the case the "Adaptive Decision Making" step is performed.

FIG. 11 also illustrates the operation of the feedback signal F to the wearer. It should be noted that the feedback signal F is fed back to the wearer in the "Feedback Generator" step.

The prosthesis 10a, 10b of the present invention provides the wearer the flexibility of commanding a large number of different grip patterns (operating modes and parameters) by the provision of a single input command signal. With known prostheses, if a wearer wishes to select or change grip pattern they typically have to perform a number of individual pulse or co-contraction stages, e.g. the wearer has to provide a first input command signal to select the operating mode of the digits and then has to provide a second input command signal to select the operating parameter of the digits. Operating a prosthesis in this manner is time consuming, frustrating and tiring. The prosthesis 10a, 10b of the present invention solves this problem by allowing the operating mode and operating parameter(s) to be selected by a single input command signal.

Modification and improvements may be made to the above without departing from the scope of the present invention. For example, although the prosthesis 10a has been illustrated and described above has having two digits (thumb digit 12a and forefinger digit 12b), it should be appreciated that the prosthesis 10a may have more than two digits 12.

Furthermore, although the moveable component has mainly been referred to above as the digits 12, is should be appreciated that the moveable component may include the body part 14 to which the digits 12 are attached.

Also, although the present invention has principally been described as a prosthesis, it should also be appreciated that the invention could also be described, and is applicable to, an orthosis. That is, a further aspect of the present invention is an orthosis comprising: at least one moveable component, wherein the at least one moveable component has two or more operating modes and at least one operating parameter; and an electronic device operable to select both an operating mode of the at least one moveable component and at least one operating parameter of the at least one moveable component in response to an input command signal from the wearer of the prosthesis.

In this arrangement, the digits may be toes.

Furthermore, although the input control signals p1, p2 etc. have been described above as coming from EMG control signals 20, it should be appreciated that the input signals from the wearer of the prosthesis may be provided via one or more switches. The switches may be analogue or digital switches. The switches may be actuated by residual movement of the wearer of the prosthesis, wrist and/or shoulder movement of the wearer of the prosthesis, movement of the remnant digits and/or knuckles, or the like. The input signals from the wearer of the prosthesis may be provided by electrophysiological signals derived from the activity of, or from, surface electromyographic (EMG) and intramuscular activity of residual muscle actions of the wearer of the prosthesis, electroneurographic (ENG) activity of residual peripheral nerves of the wearer of the prosthesis, pressure sensitive resistors on the wearer of the prosthesis, signals derived from one or more neural implants in the wearer of the prosthesis implanted in the brain or spinal cord, EMG activity from reinnervated muscles, muscles of the feet and/or chest, or the like. The input signals from the wearer of the prosthesis may be provided by non-electrophysiological signals derived from the activity pressure or bend sensitive resistors on the wearer of the body to capture any residual movement digits, wrist, elbow or shoulder of the wearer of the prosthesis or the like. The input signals from the wearer of the prosthesis may be provided by signals derived from the activity of, or from, electromyographic (EMG) activity of hand muscle actions, or residual muscle actions, of the wearer of the prosthesis recorded non-invasively from the skin or invasively from deep muscular structures. The prosthesis may be controlled by the activity of any combination of intrinsic and extrinsic hand muscle group, such as muscles in the thenar and hypothenar muscles, the interossei muscles originating between the metacarpal bones, the long flexors and extensors in the forearm, e.g. extensor pollicis longus muscle, extensor/flexor indicis muscle, or the like.

Also, it should be appreciated that the input control signals p1, p2 etc. may be produced from any combination of the above-referenced input signal options.

Furthermore, although the electronic device has been described above as being operable to select both an operating mode and an operating parameter(s) of the digits in response to an input command signal from the wearer, it should be appreciated that the electronic device may be operable to select one or more sequences of operating modes and operating parameter(s) of the digits in response to an input command signal from the wearer. This would allow the wearer to perform, for example, a number of tasks in a chosen order, such as the gesture point of FIG. 2 followed by the gesture wave of FIG. 8.

The invention claimed is:

1. A method of operating a prosthesis having at least one moveable digit and an electronic control device, the method comprising:
receiving a first input control signal from a first myoelectric electrode, wherein the first input control signal is based at least in part on a first myoelectric signal received at the first myoelectric electrode from a first muscle of a wearer of the prosthesis;
receiving a second input control signal from a second myoelectric electrode, wherein the second input control signal is based at least in part on a second myoelectric signal received at the second myoelectric electrode from a second muscle of the wearer of the prosthesis, wherein the second muscle is different from the first muscle;
processing, using the electronic control device, at least the first and second input control signals to determine a single input command signal based at least in part on a magnitude of the first and second input control signals;

comparing, using the electronic control device, the single input command signal with an operating profile stored in the electronic control device to identify a range of the operating profile that corresponds to the single input command signal, wherein the operating profile is characterized by a plurality of ranges including the identified range, each range of the plurality of ranges corresponding to a different combination of a hand gesture of at least three hand gestures of the at least one moveable digit of the prosthesis and a magnitude of a plurality of magnitudes of an operating parameter of the at least one moveable digit of the prosthesis, wherein the operating parameter comprises at least one of speed, acceleration, deceleration, applied force, operating duration, amount of extension, amount of flexion, or angle of rotation;

simultaneously determining a selected hand gesture from the at least three hand gestures that corresponds to the identified range and a selected magnitude of the operating parameter from the plurality of magnitudes that corresponds to the identified range; and instructing the at least one moveable digit to perform a digit movement corresponding to the selected hand gesture at or with the selected magnitude of the operating parameter, wherein the electronic control device can instruct the at least one moveable digit to transition directly from a first hand gesture of the at least three hand gestures to any other hand gesture of the at least three hand gestures based at least in part on said comparing.

2. The method of claim 1, further comprising sending a feedback signal to the wearer of the prosthesis, the feedback signal indicative of the selected hand gesture and the selected magnitude of the operating parameter.

3. The method of claim 1, wherein the operating profile is visually displayed on a screen and is divided into a plurality of regions located between a first axis and a second axis, each region representing a separate combination of a hand gesture of the at least three hand gestures and a magnitude of the plurality of magnitudes of the operating parameter, and wherein said comparing further comprises identifying a region of the plurality of regions that includes the single input command signal, and wherein said simultaneously determining comprises selecting the hand gesture and operating parameter associated with the identified region.

4. The method of claim 1, wherein each of the first and second input control signals is modified in response to a recorded signal of a mathematical operation on at least one of an electrophysiological or non-electrophysiological measurement from the wearer of the prosthesis.

5. The method of claim 1, wherein the electronic control device is operable to modify the operating profile stored in the electronic control device to a modified operating profile.

6. The method of claim 1, further comprising pre-processing at least one of the first or second input control signals from the wearer of the prosthesis to predict an intended input command signal.

7. The method of claim 1, wherein the selected hand gesture comprises open, close, pinch, point, grasp or wave.

8. The method of claim 1, wherein the at least three hand gestures comprises at least four hand gestures.

9. A method of operating a prosthesis having at least one moveable digit, the at least one moveable digit and an electronic device, the method comprising:

determining, using the electronic device, a single input command signal based at least in part on a first input control signal received from a first myoelectric electrode and a second input control signal received from a second myoelectric electrode; and selecting, using the electronic device, a particular hand gesture from at least three hands gestures of the at least one moveable digit of the prosthesis and a particular magnitude of a plurality of magnitudes of an operating parameter, wherein said selecting comprises:

comparing the single input command signal with an operating profile stored in an electronic control device to identify a particular range of the operating profile that corresponds to the single input command signal, wherein the operating profile is characterized by a plurality of ranges including the identified range, each range of the plurality of ranges corresponding to a different combination of a hand gesture of the at least three hand gestures and a magnitude of the plurality of magnitudes of the operating parameter, and identifying the particular hand gesture and the particular magnitude for selection in response to identifying the particular range; and causing the at least one moveable digit to perform a digit movement corresponding to the particular hand gesture at or with the particular magnitude of the operating parameter, wherein the electronic control device can cause the at least one moveable digit to transition directly from any other hand gesture of the at least three hand gestures to the particular hand gesture based at least in part on said selecting.

10. The method of claim 9, further comprising outputting at least one of an output signal indicative of the particular hand gesture or the particular magnitude of the operating parameter.

11. The method of claim 10, wherein the output signal is communicated to a wearer of the prosthesis visually, kinaesthetically, aurally or neurally.

12. The method of claim 10, wherein the output signal is communicated non-invasively to a wearer of the prosthesis via electro-tactile or vibro-tactile stimulation of skin of the body of the wearer of the prosthesis.

13. The method of claim 9, wherein the particular hand gesture comprises open, close, pinch, point, grasp or wave.

14. The method of claim 9, wherein the operating parameter comprises speed, acceleration, deceleration, applied force, operating duration, amount of extension, amount of flexion, or angle of rotation associated with the particular hand gesture.

15. The method of claim 9, further comprising:

receiving the first input control signal from the first myoelectric electrode, wherein the first input control signal is based at least in part on a first myoelectric signal received at the first myoelectric electrode from a first muscle of a wearer of the prosthesis; and receiving the second input control signal from the second myoelectric electrode, wherein the second input control signal is based at least in part on a second myoelectric signal received at the second myoelectric electrode from a second muscle of the wearer of the prosthesis, wherein the second muscle is different from the first muscle.

16. The method of claim 9, wherein the at least three hand gestures comprises at least four hand gestures.

* * * * *